US008165517B2

(12) United States Patent
Fitzgerald et al.

(10) Patent No.: US 8,165,517 B2
(45) Date of Patent: Apr. 24, 2012

(54) METHODS FOR IDENTIFYING INHIBITORS OF VASCULAR INJURY

(75) Inventors: Garrett A. Fitzgerald, Wayne, PA (US); Lei Zhao, Chester Springs, PA (US)

(73) Assignee: The Trustees of the University of Pennsylvania, Philadelphia ( * ) Notice: Subject to any disclaimer, the term of this patent is extended or adjusted under 35 U.S.C. 154(b) by 447 days.

(21) Appl. No.: 11/814,360

(22) PCT Filed: Jan. 19, 2006

(86) PCT No.: PCT/US2006/001834
§ 371 (c)(1),
(2), (4) Date: Jun. 4, 2008

(87) PCT Pub. No.: WO2006/078776
PCT Pub. Date: Jul. 27, 2006

(65) Prior Publication Data
US 2008/0286203 A1 Nov. 20, 2008

Related U.S. Application Data

(60) Provisional application No. 60/645,418, filed on Jan. 19, 2005.

(51) Int. Cl.
*C12Q 1/00* (2006.01)
*C12Q 1/25* (2006.01)
(52) U.S. Cl. .............. 434/4; 435/7.1; 435/7.2; 435/7.21
(58) Field of Classification Search .................. None
See application file for complete search history.

(56) References Cited

U.S. PATENT DOCUMENTS

| | | | |
|---|---|---|---|
| 4,741,900 A | 5/1988 | Alvarez et al. | |
| 5,314,995 A | 5/1994 | Fell, Jr. et al. | |
| 5,545,403 A | 8/1996 | Page et al. | |
| 5,545,405 A | 8/1996 | Page et al. | |
| 5,637,677 A | 6/1997 | Greene et al. | |
| 5,998,144 A | 12/1999 | Reff et al. | |
| 6,075,181 A | 6/2000 | Kucherlapati et al. | |
| 6,091,001 A | 7/2000 | Jakobovits et al. | |
| 6,114,598 A | 9/2000 | Kucherlapati et al. | |
| 6,878,522 B2 * | 4/2005 | Li et al. ........................... | 435/7.1 |
| 2003/0091982 A1 | 5/2003 | Zong | |
| 2003/0129176 A1 * | 7/2003 | Jones et al. ................... | 424/94.1 |

FOREIGN PATENT DOCUMENTS

| | | |
|---|---|---|
| EP | 0396387 | 1/1990 |
| WO | 89/12624 | 12/1989 |
| WO | 91/14438 | 10/1991 |
| WO | 92/08495 | 5/1992 |
| WO | 2004/010957 | 5/2004 |

OTHER PUBLICATIONS

Mandal et al., Uteroglobin represses allergen-induced inflammatory response by blocking PGD2 receptor-mediated functions. Journal of Experimental Medicine 199(10):1317-1330, May 17, 2004.*
Matsuoka et al., Prostaglandin D2 as a mediator of allergic asthma. Science 287:2013-2017, 2000.*
Arimura et al., Prevention of allergic inflammation by a novel prostaglandin receptor antagonist, S-5751. Journal of Pharmacology and Experimental Therapeutics 298:411-419, 2001.*
Ross R., "Atherosclerosis—an inflammatory disease," N. Engl. J. Med. (1999); 340(2); 115-26.
Egan, S.E., et al., "The pathway to signal achievement," Nature (1993) 365: 781-783.
Kyte, J., et al., "A simple method for displaying the hydropathic character of a protein," J. Mol. Biol. (1982) 157(1):105-132.
Hopp, T.P., et al. "Prediction of protein antigenic determinants from amino acid sequences," Proc. Natl. Acad. Sci. USA (1981) 78(6):3824-3828.
Hopp, T.J., et al., "A computer program for predicting protein antigenic determinants," Mol. Immunol. (1983) 20(4):483-489.
Hopp, T.J., et al., "Protein surface analysis. Methods for identifying antigenic determinants and other interaction sites," J. Immunol. Methods (1986) 88(1):1-18.
Jameson, B.A., et al. "The antigenic index: a novel algorithm for predicting antigenic determinants," Comput. APpl. Biosci. (1988) 4(1):181-186.
Emini, E.A., et al., "Antigenic conservation and divergence between the viral-specific proteins of poliovirus type 1 and various picornaviruses," Virology (1985) 140(1):13-20.
McCafferty, J. et al., "Phage antibodies: filamentous phage displaying antibody variable domains," Nature (1990) 348:552-554.
Clackson et al., "Making antibody fragments using phage display libraries," Nature (1991) 352(6336):624-628.
Marks, et al., "By-passing immunization. Human antibodies from V-gene libraries displayed on phage," J. Mol. Biol. (1991) 222(3):581-597.
Kohler, et al., "Continuous cultures of fused cells secreting antibody of predefined specificity", Nature (1975) 256:495-496.
Scatchard, "The attractions of proteins for small molecules and ions", Ann. NY Acad, Sci. (1949) 51: 660-672.
Accession No. NM_008962, Aug. 25, 2004.
Hirata, et al., "Molecular characterization of a mouse prostaglandin D receptor and functional expression of the cloned gene," Proc. Natl. Acad. Sci. USA (1994) 91(23):11192-11196.
Accession No. NM_000953, Jan. 3, 2005.
Boie, et al. "Molecular cloning and characterization of the human prostanoid DP receptor," J. Biol. Chem. (1995) 270 (32):18910-18916.

* cited by examiner

Primary Examiner — Ruixiang Li
(74) Attorney, Agent, or Firm — Pepper Hamilton, LLP

(57) ABSTRACT

The present invention provides, inter alia, inhibitors of cardiovascular diseases and disorders. The present invention also provides therapeutic methods for preventing and/or treating cardiovascular diseases and disorders. Further, the present invention provides methods of identifying inhibitors of cardiovascular diseases and disorders as well as model systems suitable for identifying such inhibitors as well as methods and compositions for detecting and/or diagnosing cardiovascular diseases and disorders.

25 Claims, 8 Drawing Sheets

SEQUENCE LISTING

```
<160> NUMBER OF SEQ ID NOS: 4

<210> SEQ ID NO 1
<211> LENGTH: 3190
<212> TYPE: DNA
<213> ORGANISM: Homo sapiens

<400> SEQUENCE: 1
tgccaccagt ggagctctct ctgctgcaca acctctgtgc cttagctgcg ccctgagcag      60 cctgggctc cttcacagcg ggcctggctg cagccttttct tccagtcaga cgggacaagg     120
gctatgaacg agtcctatcg ctgtcagaca tccacctggg tggaaagggg ctcctcggcg     180
acgatgggcg ctgtgctctt cggtgcgggg cttctgggca atcttctggc gctggtgctg     240
ctggcgcgct cgggactggg gtcttgccgg ccagggccac tacacccgcc gccctcggtc     300
ttttatgtgc tcgtgtgtgg cttgacggtc accgacttgc tgggcaattg tctgatcagc     360
ccgatggtcc tggctgccta cgcgcaaaac cagagcctaa aggaactgct gcctgcctca     420
ggcaatcagt tatgcgaaac gttcgccttc ctgatgtcct tctttgggct agcctcgacc     480
ttacagctgt tggctatggc ggtggagtgc tggctgtctc tgggacaccc cttcttctac     540
caaaggcacg tcaccttgcg ccggggagtg ctggtggcac cggtcgtggc cgccttctgc     600
ttggctttct gtgcgctccc cttttgctggt tttgggaagt tcgtgcagta ctgtccaggc     660
acctggtgtt tcatccagat gatccacaag gagcgttcat tttcggtaat aggcttctct     720
gtgctctact ccagcctcat ggcgctgctg gtcctcgcaa ccgtggtgtg caacctgggt     780
gccatgtaca acctctatga catgcacagg cgccagaggc actatcctca ccgctgctcc     840
agggaccgcg cccagtcagg ctcagactac aggcacgggt ccctgcatcc tttggaggag     900
ctggaccact ttgtgctgct ggctctcatg acagtgctct tcaccatgtg ttccctgcct     960
ttaatttatc gtgcgtacta tggagccttt aaacttgaga acaaagctga aggagactca    1020
gaagacctcc aagccttgcg tttcctgtct gtgatttcca tagtggaccc ctggatcttc    1080
atcatcttca ggacttcagt attccggatg ttatttcaca aggttttcac aagacctctg    1140
atctacagaa actggagcag ccattcccag caaagtaacg tggaatccac tttgtgaggg    1200 cttttgcgtgt tctgataagc tgaaaataca gcacacattc aaagagccgt gcttggaaaa    1260
gccttacaat ttaaatcctt aaaaactatc tcccatgaag agatggagag agggatcagc    1320
actgaagatc atttacttct cttccagagg acctgagttt gattcccaga acccacaaca    1380
```

```
ggtgcctcac accactgtaa gtccagctcc agggaatctt acaccagtgg cctgcacggt      1440
cacctgcact catgtgcata taaccacatg tgagcacaca cacacacaca cagtgagaga      1500
gagagagaga gagagagaca gagagagaga gacagagaga gagggagaga gacttaaaag      1560
taataaaagc taatttaaaa tatctcccat aattaagaca tctcaaaggt aaccaattta      1620
tatgttgtca ctctgtatcc ataaacccctt ttggtccatt taaaaaaatg tgctattaac     1680
agcaattaaa ctttgtatgt tataaacaat gttaacagtg ctatagcaat gattttaatt     1740
gtctcaacat ttgtacctga tggttctaaa tgtttagggc aatcttgaga cccatgggtt     1800
tttaattgaa atatgataga acaacaccg tctcactgta ggcttgtaat tttgtagtgg      1860
gtattcttga acaaacctag caacatctca cacattgtta cagtaaagct taacttattt     1920
tgtatcattg ttgctccttt ttgtggatgg tttggtttgg tttgtttgtt tgttttttgtc    1980 aaatgaccta agaataatct gaattgtaga taatatttaa gagaaatgag ttgggaaacc    2040
agatcaggta aggtatttgg agagaccatt tcggggcta caggaaaaga cctgcaagtc     2100
ccatgtagtt aaatgaaaca agatataact agggtcaaca actcaaagtg gaaaaggaa     2160 actgatcttt tgaagtctgg tctggaagca gggatggcaa gggtagtcag taatttgcat   2220
aatgagtcta agattttcaa ttcaggaaac cttcattttc acattgatgg actctttaaa    2280
gagcaggatt tgtgttttctt gggaaaacac tggtgtatga cttaccgaag agctgtatta   2340
tataccaatt tcagtcaact cacagggcat tgagcacagt aggaggccca ctcaggacat    2400
agcctctgtg aagggtgatg gcagtggcat tcacacctgc ctcttacagc ttcagtctgc   2460
tgttagtaga gggaatgaga tgttacctgg gactgcagtg agctgggcta gctgaaccag   2520
agtaaaaaca gctctgaaag gcactgggaa cactttaatt actcactttt gaggtcacac   2580
aggccagcaa cactataacc taaaagaaa atgtgtgggg tgtgcggtgg gagatgggga   2640
gtacccctgc attgggagag agctggagct cacagcaaga gctttggaca gctataaagc   2700
agtagatggg gataggagag agtttccgag tccctgagca ttccgacact cagatgctgg   2760
aatggacgca aggtctgcag caggcagttc ctctcaaaga caagaggagc tcccatattt   2820
cttggtcagc agaaaaccaa ttttctcaac tctcattttc ctgagacctc agagatggta   2880
ttaacttagc ttatgtatct atgtatgtat gtatgtatgc atgtatgtac gtacatagag   2940
caaaactgtg aaaaagccaa attaggaata aagaaagtat aaactgagag tatgacacaa   3000
agaaaaatgt tttggttttg gtttaacttg tgtttctatg tttaatgtga atgatgattt   3060 ttttttttctt ttggtctgag gaggtgcatt ttttttcgtgt gtgtgtccta gttttagaag    3120
gtatgctatg gtaactgtct agagaatttg ataaagtgcc agatgaatca ataaatgtga    3180
tttttataag                                                             3190
```

<210> SEQ ID NO 2
<211> LENGTH: 357
<212> TYPE: PRT
<213> ORGANISM: Homo sapiens

<400> SEQUENCE: 2

Met Asn Glu Ser Tyr Arg Cys Gln Thr Ser Thr Trp Val Glu Arg Gly
1               5                   10                  15

Ser Ser Ala Thr Met Gly Ala Val Leu Phe Gly Ala Gly Leu Leu Gly
            20                  25                  30

Asn Leu Leu Ala Leu Val Leu Leu Ala Arg Ser Gly Leu Gly Ser Cys
        35                  40                  45

```
Arg Pro Gly Pro Leu His Pro Pro Ser Val Phe Tyr Val Leu Val
    50                  55                  60

Cys Gly Leu Thr Val Thr Asp Leu Leu Gly Asn Cys Leu Ile Ser Pro
 65                  70                  75                  80

Met Val Leu Ala Ala Tyr Ala Gln Asn Gln Ser Leu Lys Glu Leu Leu
                 85                  90                  95

Pro Ala Ser Gly Asn Gln Leu Cys Glu Thr Phe Ala Phe Leu Met Ser
                100                 105                 110

Phe Phe Gly Leu Ala Ser Thr Leu Gln Leu Leu Ala Met Ala Val Glu
            115                 120                 125

Cys Trp Leu Ser Leu Gly His Pro Phe Phe Tyr Gln Arg His Val Thr
    130                 135                 140

Leu Arg Arg Gly Val Leu Val Ala Pro Val Val Ala Ala Phe Cys Leu
145                 150                 155                 160

Ala Phe Cys Ala Leu Pro Phe Ala Gly Phe Gly Lys Phe Val Gln Tyr
                165                 170                 175

Cys Pro Gly Thr Trp Cys Phe Ile Gln Met Ile His Lys Glu Arg Ser
                180                 185                 190

Phe Ser Val Ile Gly Phe Ser Val Leu Tyr Ser Ser Leu Met Ala Leu
            195                 200                 205

Leu Val Leu Ala Thr Val Val Cys Asn Leu Gly Ala Met Tyr Asn Leu
    210                 215                 220

Tyr Asp Met His Arg Arg Gln Arg His Tyr Pro His Arg Cys Ser Arg
225                 230                 235                 240

Asp Arg Ala Gln Ser Gly Ser Asp Tyr Arg His Gly Ser Leu His Pro
                245                 250                 255

Leu Glu Glu Leu Asp His Phe Val Leu Leu Ala Leu Met Thr Val Leu
                260                 265                 270

Phe Thr Met Cys Ser Leu Pro Leu Ile Tyr Arg Ala Tyr Tyr Gly Ala
            275                 280                 285

Phe Lys Leu Glu Asn Lys Ala Glu Gly Asp Ser Glu Asp Leu Gln Ala
    290                 295                 300

Leu Arg Phe Leu Ser Val Ile Ser Ile Val Asp Pro Trp Ile Phe Ile
305                 310                 315                 320

Ile Phe Arg Thr Ser Val Phe Arg Met Leu Phe His Lys Val Phe Thr
                325                 330                 335

Arg Pro Leu Ile Tyr Arg Asn Trp Ser Ser His Ser Gln Gln Ser Asn
                340                 345                 350

Val Glu Ser Thr Leu
        355

<210> SEQ ID NO 3
<211> LENGTH: 2966
<212> TYPE: DNA
<213> ORGANISM: Homo sapiens

<400> SEQUENCE: 3
cgcccgagcc gcgcgcggag ctgccggggg ctccttagca cccgggcgcc ggggccctcg     60
cccttccgca gccttcactc cagccctctg ctcccgcacg ccatgaagtc gccgttctac    120
cgctgccaga acaccaccct gtgtggaaaa ggcaactcgg cggtgatggg cggggtgctc    180
ttcagcaccg gcctcctggg caacctgctg gccctggggc tgctggcgcg ctcggggctg    240
gggtggtgct cgcggcgtcc actgcgcccg ctgcctcgg tcttctacat gctggtgtgt    300
ggcctgacgg tcaccgactt gctgggcaag tgcctcctaa gcccggtggt gctggctgcc    360
```

```
tacgctcaga accggagtct gcgggtgctt gcgcccgcat tggacaactc gttgtgccaa      420
gccttcgcct tcttcatgtc cttctttggg ctctcctcga cactgcaact cctggccatg      480
gcactggagt gctggctctc cctagggcac ccttcttct accgacggca catcaccctg       540
cgcctgggcg cactggtggc cccggtggtg agcgccttct ccctggcttt ctgcgcgcta      600
cctttcatgg gcttcgggaa gttcgtgcag tactgccccg gcacctggtg ctttatccag      660
atggtccacg aggagggctc gctgtcgtg ctggggtact ctgtgctcta ctccagcctc       720
atggcgctgc tggtcctcgc caccgtgctg tgcaacctcg gcgccatgcg caacctctat      780
gcgatgcacc ggcggctgca gcggcacccg cgctcctgca ccagggactg tgccgagccg      840
cgcgcggacg ggagggaagc gtcccctcag cccctggagg agctggatca cctcctgctg      900
ctggcgctga tgaccgtgct cttcactatg tgttctctgc ccgtaattta tcgcgcttac      960
tatggagcat ttaaggatgt caaggagaaa acaggacct ctgaagaagc agaagacctc      1020
cgagccttgc gatttctatc tgtgatttca attgtggacc cttggatttt tatcatttc       1080 agatctccag tatttcggat attttttcac aagattttca ttagacctct taggtacagg     1140
agccggtgca gcaattccac taacatggaa tccagtctgt gacagtgttt ttcactctgt     1200
ggtaagctga ggaatatgtc acatttcag tcaaagaacc atgattaaaa aaaaaagac      1260 aacttacaat ttaaatcctt aaaagttacc tcccataaca aaagcatgta tatgtatttt     1320
caaaagtatt tgatatctta caatgtgtt accattctat agtcatgaac cccttcagtg      1380
cattttcatt tttttatta cagcaactaa aatttatat attgtaacca gtgttaaaag      1440
tcttaaaaaa caatggtat aattgtccct acatttgtgc ttggtggccc tatttttttt      1500
ttttagagag gccttgagac atacaggtct tttaaaatac agtagaaaca ccactgttta    1560
cgattatacg atggacattc ataaaaagca taatttctta ccctattcat tttttggtga     1620
aacctgattc attgattta tatcattgcc gatgttagt tcatttctt gccaattgat      1680 ctaagcatag cctgaattat gatgttcctc agagaagtga ggtgggaaat atgaccaggt     1740
caggcagttg gagggcttc cccagccacc atcggggagt acttgctgcc tcaggtggag      1800
acctgaagct gtaactagat gcagagcaag atatgactat agcccacaac ccaaagaagc     1860
aaaaattcgt ttttatcttt tgaaatccag tttctttgt attgagtcaa gggtgtcagt     1920
aggaatcaaa agttggggt gggttgcaaa atgttctttc agtttttaga acctccattt      1980 tataaagaa ttatcctatc aatggattct ttagtggaag gatttatgct tctttgaaaa       2040
ccagtgtgtg actcactgta gagccatgtt tactgtttga ctgtgtggca caggggggca     2100
tttggcacag caaaaagccc acccaggact tagcctcagt tgacgatagt aacaatggcc     2160
ttaacatcta ccttaacagc taccattac agccgtattc tgctgtccgt ggagacggta      2220
agatcttagg ttccaagatt ttacttcaaa ttacacctc aaaactggag cagcatatag       2280
ccgaaaagga gcacaactga gcactttaat agtaatttaa agttttcaa gggtcagcaa      2340 tatgatgact gaaagggaaa agtggaggaa acgcagctgc aactgaagcg gagactctaa     2400
acccagcttg caggtaagag ctttcacctt tggtaaaaga acagctgggg aggttcaagg     2460
ggtttcagca tctctggagt tcctttgtat ctgacaatct caggactcca aggtgcaaag     2520
cctgctgcat ttgcgtgatc tcaagacctc cagccagaag tcccttccaa atataagagt     2580
actcatgttt atttattcc aactgagcag caacctcctt tgtttcactt atgttttttc      2640
cagtatctga gataatataa agctgggtaa tttttatgt aatttttgg tatagcaaaa       2700 ctgtgaaaaa gccaaattag gcatacaagg agtatgattt aacagtatga catgatgaaa     2760
```

-continued

```
aaaatacagt tgtttttgaa atttaacttt tgtttgtacc ttcaatgtgt aagtacatgc    2820
atgttttatt gtcagaggaa gaacatgttt tttgtattct ttttttggag aggtgtgtta    2880
ggataattgt ccagttaatt tgaaaaggcc ccagatgaat caataaatat aattttatag    2940
taaaaaaaaa aaaaaaaaaa aaaaaa                                         2966
```

<210> SEQ ID NO 4
<211> LENGTH: 359
<212> TYPE: PRT
<213> ORGANISM: Homo sapiens

<400> SEQUENCE: 4

```
Met Lys Ser Pro Phe Tyr Arg Cys Gln Asn Thr Thr Ser Val Glu Lys
1               5                   10                  15

Gly Asn Ser Ala Val Met Gly Gly Val Leu Phe Ser Thr Gly Leu Leu
            20                  25                  30

Gly Asn Leu Leu Ala Leu Gly Leu Leu Ala Arg Ser Gly Leu Gly Trp
        35                  40                  45

Cys Ser Arg Arg Pro Leu Arg Pro Leu Pro Ser Val Phe Tyr Met Leu
    50                  55                  60

Val Cys Gly Leu Thr Val Thr Asp Leu Leu Gly Lys Cys Leu Leu Ser
65                  70                  75                  80

Pro Val Val Leu Ala Ala Tyr Ala Gln Asn Arg Ser Leu Arg Val Leu
                85                  90                  95

Ala Pro Ala Leu Asp Asn Ser Leu Cys Gln Ala Phe Ala Phe Phe Met
            100                 105                 110

Ser Phe Phe Gly Leu Ser Ser Thr Leu Gln Leu Leu Ala Met Ala Leu
        115                 120                 125

Glu Cys Trp Leu Ser Leu Gly His Pro Phe Phe Tyr Arg Arg His Ile
    130                 135                 140

Thr Leu Arg Leu Gly Ala Leu Val Ala Pro Val Val Ser Ala Phe Ser
145                 150                 155                 160

Leu Ala Phe Cys Ala Leu Pro Phe Met Gly Phe Gly Lys Phe Val Gln
                165                 170                 175

Tyr Cys Pro Gly Thr Trp Cys Phe Ile Gln Met Val His Glu Glu Gly
            180                 185                 190

Ser Leu Ser Val Leu Gly Tyr Ser Val Leu Tyr Ser Ser Leu Met Ala
        195                 200                 205

Leu Leu Val Leu Ala Thr Val Leu Cys Asn Leu Gly Ala Met Arg Asn
    210                 215                 220

Leu Tyr Ala Met His Arg Arg Leu Gln Arg His Pro Arg Ser Cys Thr
225                 230                 235                 240

Arg Asp Cys Ala Glu Pro Arg Ala Asp Gly Arg Glu Ala Ser Pro Gln
                245                 250                 255

Pro Leu Glu Glu Leu Asp His Leu Leu Leu Leu Ala Leu Met Thr Val
            260                 265                 270

Leu Phe Thr Met Cys Ser Leu Pro Val Ile Tyr Arg Ala Tyr Tyr Gly
        275                 280                 285

Ala Phe Lys Asp Val Lys Glu Lys Asn Arg Thr Ser Glu Glu Ala Glu
    290                 295                 300

Asp Leu Arg Ala Leu Arg Phe Leu Ser Val Ile Ser Ile Val Asp Pro
305                 310                 315                 320

Trp Ile Phe Ile Ile Phe Arg Ser Pro Val Phe Arg Ile Phe Phe His
                325                 330                 335
```

-continued

```
Lys Ile Phe Ile Arg Pro Leu Arg Tyr Arg Ser Arg Cys Ser Asn Ser
            340                 345                 350
Thr Asn Met Glu Ser Ser Leu
        355
```

METHODS FOR IDENTIFYING INHIBITORS OF VASCULAR INJURY

CROSS-REFERENCE TO RELATED APPLICATIONS

This application is the U.S. National Stage filing of International Application Serial No. PCT/US2006/001834 filed Jan. 19, 2006, which claims priority to U.S. Provisional Patent Application No. 60/645,418, filed Jan. 19, 2005, each of which is incorporated herein by reference in its entirety.

FIELD OF INVENTION

The present invention is directed to therapeutic methods for preventing and/or treating cardiovascular diseases and disorders and or symptoms of cardiovascular diseases and disorders. The invention is also directed to methods of identifying inhibitors of cardiovascular diseases and disorders as well as model systems suitable for identifying such inhibitors. The invention also provides methods and compositions for detecting and/or diagnosing cardiovascular diseases and disorders.

BACKGROUND OF THE INVENTION

Cardiovascular diseases and disorders remain a leading cause of morbidity and mortality in industrialized countries despite aggressive vascular intervention and a myriad blood pressure- and lipid-lowering agents. Atherosclerosis, manifested by heart disease, stroke, and peripheral vascular disease is characterized by the progressive formation of fatty streaks, stable plaques and unstable or ruptured plaques which trigger clinical complications due to intravascular thrombosis. Over the past decade, however, our understanding of atherogenesis has evolved from one of occlusive lipid accumulation to one of chronic inflammation involving cellular proliferation. (Ross R. Atherosclerosis—an inflammatory disease. N Engl J Med 1999; 340: 115-126).

Atherosclerosis is a condition in which fatty material is deposited along the walls of arteries. This fatty material thickens, hardens, and may eventually block the arteries. Atherosclerosis is characterized by thickening and hardening of artery walls wherein fat, cholesterol, and other substances accumulate in the walls of arteries and form "atheromas" or plaques. Eventually, this fatty tissue can erode the wall of the artery, diminish its elasticity (stretchiness) and interfere with blood flow. Plaques can also rupture, causing debris to migrate downstream within an artery. This is a common cause of heart attack and stroke. Clots can also form around the plaque deposits, further interfering with blood flow and posing added danger if they break off and travel to the heart, lungs, or brain.

Atherosclerosis often shows no symptoms until flow within a blood vessel has become seriously compromised. Typical symptoms of atherosclerosis include chest pain when a coronary artery is involved, or leg pain when a leg artery is involved. Sometimes symptoms occur only with exertion. In some people, however, they may occur at rest. Atherosclerosis may not be diagnosed until symptoms develop. Prior to complications, atherosclerosis may be noted by the presence of a "bruit" (a whooshing or blowing sound heard over the artery with a stethoscope). Tests that may be indicative of atherosclerosis (or complications) include, for example, abnormal differences between the blood pressure of the ankle and arm, Doppler study of the affected area, ultrasonic Duplex scanning, CT scan of the affected area, Magnetic resonance arteriography (MRA), arteriography of the affected area, intravascular ultrasound (IVUS) of the affected vessels, cardiac stress testing.

An aneurysm is a bulge in a blood vessel with the potential risk of lethally acute rupture. Typically, the blood vessel balloons to a diameter which is at least 1.5 fold larger than its normal diameter. Abdominal aorta is the most frequent site where aneurysm usually occurs. An aortic aneurysm is an aneurysm in which the aorta increases in diameter to a size at least about 1.5 times the diameter of the normal diameter of the aorta. Abdominal aortic aneurysms are characterized by medial degeneration and involve multiple processes including inflammation, immunologic cell infiltration, proteolysis. Abdominal aortic aneurysms are often, although not necessarily, associated with atherosclerosis, a chronic inflammatory disease consisting of lipid deposits into major plaques within the vessel wall.

Pain in the area of an aneurysm is a common symptom. Imaging techniques, such as X-ray, echocardiography, magnetic resonance imaging (MRI) or computed tomography (CT) scan are the common means for diagnosis. Prevention of life-threatening sudden bursts of the abdominal aorta is essentially limited to prophylactic surgery. However, elective surgery of small aneurysms (greater than two fold dilation, but smaller than 5.5 cm) does not improve survival. Therefore, interventions with drugs that target key pathogenic factors of aneurysm formation would be highly desirable.

There are several current treatments for cardiovascular diseases and disorders including aneurysms and atherosclerosis. Medications may be prescribed to reduce fats and cholesterol in the blood; a low-fat diet, weight loss, and exercise are also usually suggested. Control of high blood pressure is also important. Medications commonly prescribed include cholestyramine, colestipol, nicotinic acid, gemfibrozil, probucol, atorvastatin, lovastatin, and others. Aspirin, ticlopidine, and clopidogrel (inhibitors of platelet clumping) or anti-coagulants may be used to reduce the risk of clot formation. Balloon angioplasty uses a balloon-tipped catheter to flatten plaque and increase the blood flow past the deposits and is used to open the arteries of the heart and other arteries in the body. Another widely used technique is stenting which consists of implanting a small metal device—a stent—inside the artery (usually following angioplasty) to keep the artery open. Recently, stents have been coated with biopharmaceuticals designed to limit the proliferative response to the vascular injury of angioplasty. This proliferative response may cause a failure of response to angioplasty in up to a third of cases.

Surgically removal of deposits (endarterectomy) may be recommended in some cases. A bypass graft is the most invasive procedure, using a normal artery or vein from the patient to create a bridge that bypasses the blocked section of the artery.

Prostaglandins mediate inflammation locally and modulate physiological responses systemically. Nearly all tissues produce prostaglandins and increase production at sites of inflammation. Specifically, arachidonic acid is metabolized to prostaglandin G2 ($PGG_2$) and then to prostaglandin H2 ($PGH_2$) by cyclooxygenase. These moieties are then converted to $PGD_2$, $PGE_2$, $PGF_2$, $PGI_2$, or thromboxane.

Substantial evidence has demonstrated that COX products, such as thromboxane $A_2$ ($TxA_2$) and prostaglandin $I_2$ ($PGI_2$), play active role in atherogenesis and heart disease generally. Low dose aspirin prevents heart attack and stroke by suppressing $TxA_2$. Selective inhibitors of Cox-2 may suppress $PGI_2$ without a concomitant effect on $TxA_2$. Prostaglandin $D_2$ ($PGD_2$), a major COX metabolite, has been implicated as a pro-inflammatory lipid mediator, but also exhibits anti-inflammatory properties. The biological effects of prostaglandin D2 ($PGD_2$) are transduced by at least two 7-transmembrane G-protein coupled receptors, designated DP1 and DP2 (CRTH2). Although evidence has linked these two receptors to vascular biology and platelet function in vitro, the expression and roles of the DP1 and DP2 in the cardiovascular system in vivo and its potential role in cardiovascular disease remains unknown.

Mitogen-activated protein kinase (MAPKs) (also called extracellular signal-regulated kinases or ERKs) are rapidly activated in response to ligand binding by both growth factor receptors that are tyrosine kinases and receptors that are coupled to heterotrimeric guanine nucleotide binding proteins (G proteins) such as the thrombin receptor. The MAPKs appear to integrate multiple intracellular signals transmitted by various second messengers. MAPKs phosphorylate and regulate the activity of enzymes and transcription factors including the EGF receptor, Rsk 90, phospholipase $A_2$, c-Myc, c-Jun and Elk-1/TCF. MAPK pathways have established relevance in transmitting proliferative signals from cell membrane receptors to the nucleus.

There is a need for inhibitors of cardiovascular diseases and disorders, especially aneurysms. Similarly, there is a need for therapeutic methods for preventing and/or treating such cardiovascular diseases and disorders. There is also a need for methods of identifying inhibitors of these cardiovascular diseases and disorders as well as model systems suitable for identifying such inhibitors. A need also exists for novel methods and compositions for detecting and/or diagnosing cardiovascular diseases and disorders, especially aneurysms.

SUMMARY OF THE INVENTION

The present invention relates to methods for identifying whether a compound inhibits vascular injury. The methods comprise contacting a prostaglandin D2 receptor agonist with a model system comprising cells that express prostaglandin D2 receptors in the presence of a candidate compound, and comparing MAP kinase activity in the presence of the candidate compound to the level of MAP kinase activity in the absence of the candidate compound. An increase in the MAP kinase activity in the presence of the candidate compound indicates that the candidate compound induces MAP kinase activity A compound that does not induce MAP kinase activity is an inhibitor of vascular injury.

The present invention further relates to methods for identifying inhibitors of cardiovascular disease or disorders. In some embodiments, the methods comprise contacting prostaglandin D2 receptor agonist with a model system comprising cells that express prostaglandin D2 receptors in the presence and absence of a candidate compound and comparing the level of aortic smooth muscle cell proliferation in the presence of the candidate compound to the level aortic smooth muscle cell proliferation in the absence of the candidate compound. Inhibition of aortic smooth muscle cell proliferation in the presence of the candidate compound, is indicative of an inhibitor of atherosclerosis. In other embodiments, the methods additional or alternatively comprise contacting PDG2 or a PDG2 agonist with a cell expressing DP1 and/or DP2 receptor in the presence and absence of a candidate compound and comparing the level of DP1 and/or DP2 expression and/or activity in the presence of the candidate compound to the level of DP1 and/or DP2 expression and/or activity in the absence of the candidate compound. Inhibition of DP1 and/or DP2 expression or activity is indicative of an inhibitor of cardiovascular disease or disorders.

The present invention further relates to methods for identifying inhibitors of aneurysm comprising contacting a prostaglandin D2 receptor agonist with a model system comprising prostaglandin D2 receptors in the presence and absence of a candidate compound, and either comparing the level of aortic smooth muscle cell proliferation in the presence of the candidate compound to the level of aortic smooth muscle cell proliferation in the absence of the candidate compound, wherein inhibition of aortic smooth muscle cell proliferation is indicative of an inhibitor of aneurysm, or comparing the level of cytokine expression in the presence of the candidate compound to the level of cytokine expression in the absence of the candidate compound, wherein inhibition of cytokine expression is indicative of an inhibitor of aneurysm; or both.

The present invention additionally relates to methods of developing a prognosis for a subject who has been diagnosed with a cardiovascular disease or disorder comprising measuring levels of DP1 and/or DP2 in a sample from the subject and comparing the DP1 and/or DP2 levels to the DP1 and/or DP2 levels found in control subjects.

The present invention further relates to methods of identifying subjects at risk for aneurysm comprising measuring levels of DP1 and/or DP2 in a sample from a subject and comparing the DP1 and/or DP2 levels to DP1 and/or DP2 levels found in normal subjects, wherein elevated levels of DP1 and/or DP2 are indicative of an increased risk for aneurysm.

The present invention additionally relates to methods of imaging one or more aneurysms in a subject comprising: administering a probe, antibody or fragment thereof, or oligonucleotide that specifically binds to a DP1 or a DP2 receptor into the subject's vasculature; and determining whether the probe, antibody or fragment thereof or oligonucleotide binds to the vasculature, wherein binding of the antibody to the vasculature is indicative of the presence of one or more aneurysms.

The present invention additionally relates to methods of inhibiting a cardiovascular disease or disorder in a subject in need thereof comprising administering to said patient an amount of a DP1 and/or DP2 receptor inhibitor effective to reduce collagen disruption in a vessel of the subject and/or an amount of a DP1 and/or DP2 receptor inhibitor effective to reduce elastin disruption in a vessel of the subject.

The present invention further relates to methods A method of inhibiting an aneurysm in a subject in need thereof comprising administering to the subject a therapeutically effective dose of one or more compounds selected from the group consisting of: $PGD_2$ receptor inhibitors, inhibitors of MAP Kinase activation; MAP Kinase inhibitors; inhibitors of cytokine expression; and inhibitors of smooth muscle cell proliferation.

The present invention additionally relates to methods of inhibiting a symptom of aneurysm in a subject in need thereof comprising administering to the subject a therapeutically effective dose of one or more compounds selected from the group consisting of: $PGD_2$ receptor inhibitors, Map Kinase inhibitors, inhibitors of Map kinase activation, DP1 and/or DP2 receptor inhibitors, and inhibitors of cytokine expression.

The present invention additionally relates to methods of inhibiting smooth muscle cell proliferation comprising in a subject in need thereof comprising administering to said patient a therapeutically effective amount of one or more compounds selected from the group consisting of: DP1 receptor antagonists, DP2 receptor antagonists and Map Kinase inhibitors.

The present invention additionally relates to methods for reducing blood pressure in a subject comprising administering to said subject a therapeutically effective dose of one or more compounds selected from the group consisting of: PGD$_2$ receptor inhibitors, Map Kinase inhibitors, inhibitors of Map kinase activation, DP1 and/or DP2 receptor inhibitors, and inhibitors of cytokine expression.

BRIEF DESCRIPTION OF THE DRAWINGS

FIGS. 8A-8D are 100× magnification; FIG. 8E is 250× magnification.

DETAILED DESCRIPTION OF PREFERRED EMBODIMENTS

Definitions

Figure 1:
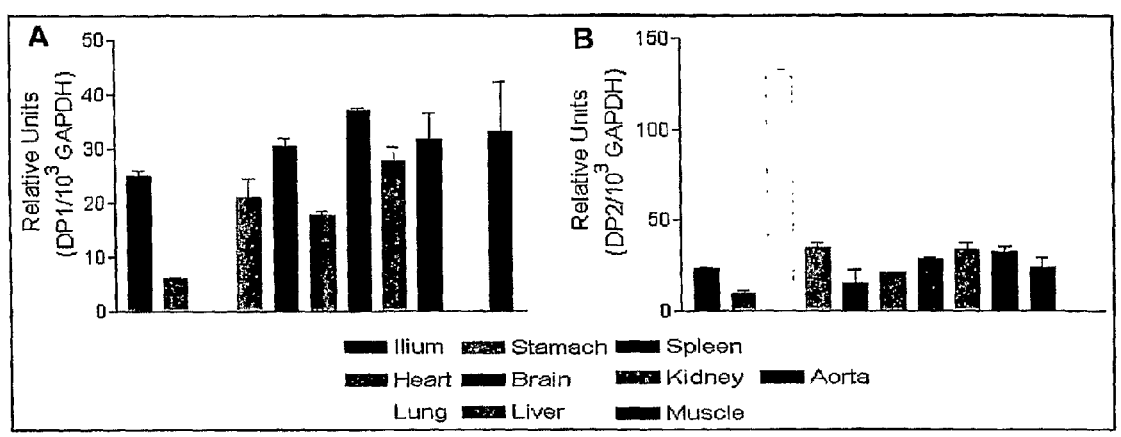
FIG. 1 depicts DP1 (A) and DP2 (B) mRNA expression in vivo in various tissues from apoE$^{-/-}$ mice fed with chow diet (8 months, n=3).

As used herein, the term "cardiovascular disease or disorder" refers to diseases or disorders affecting the circulatory system. Examples of "cardiovascular disease or disorder" include without limitation, aneurysm, stroke, dyslipidemia, hypotension, hypertension, thrombosis, myocardial infarction, cardiomyopathy or atherosclerosis. This also includes complications of treatments of cardiovascular disease, such as angioplasty or surgical intervention.

As used herein, the term "subject" refers to an animal, in some embodiments a mammal, and in some embodiments a human.

As used herein, the term "inhibit" refers to a reduction or decrease in a quality or quantity, compared to a baseline. For example, in the context of inhibition of expression, inhibition refers to a decrease in production of the gene product as compared to baseline. In some embodiments there is a reduction of about 30%, about 40%, about 50%, about 60%, about 70%, about 75%, about 80%, about 85%, about 90%, about 95%, about 99%, and about 100%. Those of ordinary skill in the art can readily the degree of inhibition.

As used herein, the term "inhibitor" refers to oligonucleotides, small molecules, mimetics, decoys, or antibodies.

As used herein, the term "antibody" refers to monoclonal and polyclonal antibodies, single chain antibodies, chimeric antibodies, bifunctional/bispecific antibodies, humanized antibodies, human antibodies, and complementary determining region (CDR)-grafted antibodies, that are specific for the target protein or fragments thereof. Antibody fragments, including Fab, Fab', F(ab')2, scfv, and Fv are also provided by the invention. Antibodies may, in some preferred embodiments, be monoclonal, humanized, primatized, single chain, or chimeric antibodies.

As used herein, the term "small molecule" refers to an organic or inorganic non-polymer compound that has a molecular weight that is less than about 10 kilodaltons. In some embodiments, the small molecule has a molecular weight that is less than about 9, about 8, about 7, about 6, about 5, about 4, about 3, about 2, about 1 kilodaltons. Examples of small molecules include peptides, oligonucleotides, organic compounds, inorganic compounds, and the like.

As used herein, the term "oligonucleotide" refers to a series of linked nucleotide residues. In some embodiments oligonucleotides are used in a polymerase chain reaction (PCR). This sequence may be based on (or designed from) a genomic sequence or cDNA sequence and is used to amplify, confirm, or detect the presence of an identical, similar, or complementary DNA or RNA in a particular cell or tissue. Oligonucleotides may also be used to modulate the expression of a gene. Oligonucleotides comprise portions of a DNA sequence and have at least about 10 nucleotides and as many as about 500 nucleotides. In some embodiments oligonucleotides comprise from about 10 nucleotides to about 50 nucleotides, from about 15 nucleotides to about 30 nucleotides, and from about 20 nucleotides to about 25 nucleotides. Oligonucleotides may be chemically synthesized and can also be used as probes. In some embodiments oligonucleotides are single stranded. In some embodiments oligonucleotides comprise at least one portion which is double stranded. In some embodiments the oligonucleotides are antisense oligonucleotides (ASO). In some embodiments the oligonucleotides are RNA interference oligonucleotides (RNAi oligonucleotides).

As used herein, the term "decoy receptor" refers to a receptor comprising at least a portion of a polypeptide, mimetic, or other macromolecule capable of binding PDG2 and/or a PDG2 agonist. In some embodiments, the decoy receptor comprises at least a portion of a DP1 and/or DP2 receptor. In some embodiments the decoy receptor competes with natural DP1 and/or DP2 receptors for PDG2 and/or a PDG2 agonist. In some embodiments, the decoy receptor is labeled to facilitate quantification, qualification, and/or visualization. In other embodiments, the decoy receptor further comprises a moiety to facilitate isolation and/or separation of the decoy receptor and or the decoy receptor-PDG2 complex. In some embodiments, the decoy receptor is a non-signaling molecule which functions by capturing PDG2 and preventing it from interacting with the signaling DP1 and/or DP2 receptor. In some embodiments the decoy receptor comprises at least a portion of a DP1 and/or DP2 receptor fused to an antibody or antibody fragment.

As used herein, the term "mimetic" is used to refer to compounds which mimic the activity of a peptide. Mimetics are non-peptides but may comprise amino acids linked by non-peptide bonds. U.S. Pat. No. 5,637,677, issued on Jun. 10, 1997, and parent applications thereof, all of which are incorporated herein by reference, contain detailed guidance on the production of mimetics. Briefly, the three-dimensional structure of the peptides which specifically interacts with the three dimensional structure of the DP1 receptor is duplicated by a molecule that is not a peptide.

As used herein, the term "MAP kinase" includes refers to mitogen-activated protein (MAP) kinases. MAP kinases regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) Nature 365:781-783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1). MAP kinases include, without limitation, ERKs (ERK 1/2/5), SAPKs, JNKs (1/2/3) and BMKs.

As used herein, the term "therapeutically effective amount" is meant an amount of a compound of the present invention effective to yield the desired therapeutic response. The specific therapeutically effective amount will, obviously, vary with such factors as the particular condition being treated, the physical condition of the patient, the type of mammal or animal being treated, the duration of the treatment, the nature of concurrent therapy (if any), and the specific formulations employed and the structure of the compounds or its derivatives. In some embodiments, in the context of treating a cardiovascular disease or disorder, the term "therapeutically effective amount" refers to an amount inhibitor that reduces or stabilizes or regresses plaque formation or an amount that reduces or stabilizes or regresses any form of vascular proliferation which can cause blood vessel obstruction. It may also be an amount that elevates or reduces blood pressure to a degree consistent with an improvement in health. In some embodiments, "therapeutically effective amount" refers to an amount of a compound of the present invention effective to inhibit, treat or diagnose one or more aneurysms.

As used herein, the term "prophylactically effective amount" is meant to refer to an amount of an antibody, peptide, or mimetic which produces a medicinal effect observed as the prevention of non-transformed cells from becoming transformed in an individual when a prophylactically effective amount of an antibody, peptide or mimetic is administered to an individual. Prophylactically effective amounts are typically determined by the effect they have compared to the effect observed when a composition which includes no active ingredient is administered to a similarly situated individual.

As used herein, the phrase "injectable pharmaceutical composition", or variants thereof, refers to pharmaceutical compositions which satisfy the USP requirements for "injectables", i.e., sterile, pyrogen- and particulate free, and possessing specific pH and isotonicity values.

As used herein "combination therapy" means that the individual in need of treatment is given another drug for the cardiovascular disease or disorder in conjunction with the methods and/or inhibitors of the present invention. This combination therapy can be sequential therapy where the individual is treated first with one or more drugs and then the other or two or more drugs are given simultaneously.

As used herein, the term "detecting" means to establish, discover, or ascertain evidence of an activity (for example, gene expression) or biomolecule (for example, a polypeptide). Methods of detection are well known to those of skill in the art. For example, methods of detecting polynucleotides include, but are not limited to PCR, Northern blotting, Southern blotting, RNA protection, and DNA hybridization (including in situ hybridization). Methods of detecting polypeptides include, but are not limited to, Western blotting, ELISA, enzyme activity assays, slot blotting, peptide mass fingerprinting, electrophoresis, and immunochemistry, and immunohistochemistry. Other examples of detection methods include, but are not limited to, radioimmunoassay (RIA), chemiluminescence immunoassay, fluoroimmunoassay, time-resolved fluoroimmunoassay (TR-FIA), two color fluorescent microscopy, or immunochromatographic assay (ICA), all well known by those of skill in the art. In some preferred embodiments of the present invention, polynucleotide expression is detected using PCR methodologies and polypeptide production is detected using ELISA technology.

As used herein, the term "binding" means the physical or chemical interaction between two or more biomolecules or compounds. Binding includes ionic, non-ionic, Hydrogen bonds, Van der Waals, hydrophobic interactions, etc. Binding can be either direct or indirect, indirect being through or due to the effects of another biomolecule or compound. Direct binding refers to interactions that do not take place through or due to the effect of another molecule or compound but instead are without other substantial chemical intermediates.

As used herein, the term "epitope" refers to an antigenic determinant of a polypeptide. In some embodiments an epitope may comprise 3 or more amino acids in a spatial conformation which is unique to the epitope. In some embodiments epitopes are linear or conformational epitopes. Generally an epitope consists of at least 4 such amino acids, and more usually, consists of at least 8-10 such amino acids. Methods of determining the spatial conformation of amino acids are known in the art, and include, for example, x-ray crystallography and 2-dimensional nuclear magnetic resonance.

As used herein the term "imaging agent" refers to a composition linked to an antibody, small molecule, or probe of the invention that can be detected using techniques known to the art-skilled. In some embodiments the imaging agent is, without limitation, $^{18}$F, $^{43}$K, $^{52}$Fe, $^{57}$Co, $^{67}$Cu, $^{67}$Ga, $^{77}$Br, $^{87}$MSr, $^{86}$Y, $^{90}$Y, $^{99}$MTc, $^{111}$In, $^{123}$I, $^{125}$I, $^{127}$Cs, $^{129}$Cs, 131I, 132I, 197Hg, $^{203}$Pb, or $^{206}$Bi.

As used herein, the term "contacting" means bringing together, either directly or indirectly, one molecule into physical proximity to a second molecule. The molecule can be in any number of buffers, salts, solutions, etc. "Contacting" includes, for example, placing a polynucleotide into a beaker, microtiter plate, cell culture flask, or a microarray, or the like, which contains a nucleic acid molecule. Contacting also includes, for example, placing an antibody into a beaker, microtiter plate, cell culture flask, or microarray, or the like, which contains a polypeptide. Contacting may take place in vivo, ex vivo, or in vitro.

As used herein, the term "probe" refers to nucleic acid sequences of variable length. In some embodiments probes comprise at least about 10 and as many as about 6,000 nucleotides. In some embodiments probes comprise at least 12, at least 14, at least 16, at least 18, at least 20, at least 25, at least 50 or at least 75 consecutive nucleotides. Probes are used in the detection of identical, similar, or complementary nucleic acid sequences. Longer length probes are usually obtained from natural or recombinant sources, are highly specific to the target sequence, and are much slower to hybridize to the target than are oligomers. Probes may be single- or double-stranded and are designed to have specificity in PCR, hybridization membrane-based, in situ hybridization (ISH), fluorescent in situ hybridization (FISH), or ELISA-like technologies.

As used herein, the term "an individual suspected of having a cardiovascular disease or disorder" refers to an individual who has not been diagnosed as being positive for one or more cardiovascular diseases or disorders but who could possibly have one or more cardiovascular diseases or disorders due to a family history, lifestyle, dietary habits, or other factors. The term "an individual suspected of having a cardiovascular disease or disorder" also includes individuals classified as being at "high-risk" for one or more cardiovascular diseases or disorders.

As used herein, the term "sample" refers to biological material from a subject. The sample assayed by the present invention is not limited to any particular type. Samples include, as non-limiting examples, single cells, multiple cells, tissues, tumors, biological fluids, biological molecules, or supernatants or extracts of any of the foregoing. Examples include tissue removed for biopsy, tissue removed during resection, blood, urine, lymph tissue, lymph fluid, cerebrospinal fluid, mucous, and stool samples. The sample used will vary based on the assay format, the detection method and the nature of the tumors, tissues, cells or extracts to be assayed. Methods for preparing samples are well known in the art and can be readily adapted in order to obtain a sample that is compatible with the method utilized. In some embodiments, the sample comprises cells or tissues from the vasculature. In some embodiments, the sample comprises at least portions of one or more veins, arteries or capillaries. In some preferred embodiments, the sample comprises cells or tissues from a subject's arteries. In some embodiments the sample comprises cells from the walls of the vasculature. In some embodiments the sample comprises cell isolated from or derived from the media lamina or the intima of the vessel. In some embodiments, the sample is not removed from the subject but is examined or tested in vivo.

Therapeutic Methods

One aspect of the present invention provides methods of inhibiting a cardiovascular disease or disorder in a subject in need thereof comprising administering to the subject a therapeutically effective dose of a DP1 and/or DP2 receptor inhibitor. In some preferred embodiments the cardiovascular disease or disorder is an aneurysm, preferably an aortic aneurysm.

The present invention also provides methods of inhibiting a cardiovascular disease or disorder in a subject in need thereof comprising administering to the subject a therapeutically effective dose of an inhibitor of MAP Kinase activation. In some preferred embodiments the cardiovascular disease or disorder is an aneurysm, preferably an aortic aneurysm.

The present invention further provides methods of inhibiting a cardiovascular disease or disorder in a subject in need thereof comprising administering to the subject a therapeutically effective dose of a MAP Kinase inhibitor. In some preferred embodiments the cardiovascular disease or disorder is an aneurysm, preferably an aortic aneurysm.

The present invention also provides methods of inhibiting a cardiovascular disease or disorder in a subject in need thereof comprising administering to the subject a therapeutically effective dose of an inhibitor of smooth muscle cell proliferation. In some preferred embodiments the cardiovascular disease or disorder is an aneurysm, preferably an aortic aneurysm.

The present invention also provides methods of inhibiting smooth muscle cell proliferation comprising in a subject in need thereof comprising administering to said patient a therapeutically effective amount of a DP1 and/or DP2 receptor inhibitor. In some embodiments the smooth muscle is aortic smooth muscle. In some embodiments, the smooth muscle is of the media lamina or intima.

The present invention also provides methods of inhibiting smooth muscle cell proliferation comprising in a subject in need thereof comprising administering to said patient a therapeutically effective amount of a Map kinase inhibitor. In some embodiments the smooth muscle is aortic smooth muscle. In some embodiments, the smooth muscle is of the media lamina or intima.

The present invention further provides methods of inhibiting a cardiovascular disease or disorder in a subject in need thereof comprising administering to the subject a therapeutically effective dose of an inhibitor of cytokine expression. In some embodiments the cytokine is selected from the group consisting of IL-1, IL-6, IL-8, IL-11, TNF-$\alpha$, IFN-$\alpha$, IFN-$\beta$, and TGF-$\beta$. In some preferred embodiments the cardiovascular disease or disorder is an aneurysm, preferably an aortic aneurysm.

The present invention also provides methods for reducing blood pressure in a subject. The methods comprise administering to the subject a Map Kinase inhibitor, an inhibitor of Map kinase activation, a DP1 and/or DP2 receptor inhibitor, or an inhibitor of cytokine expression. In some embodiments, the high blood pressure is attendant to a cardiovascular disease or disorder. In some embodiments blood pressure is reduced by 50%, 40%, 30%, 25%, 20%, 10% or 5% compared to the blood pressure of the subject prior to administration of the inhibitor.

In some embodiments the cardiovascular disease or disorder is aneurysm, stroke, dyslipidemia, hypotension, hypertension, thrombosis, myocardial infarction, cardiomyopathy or atherosclerosis. In some preferred embodiments the cardiovascular disease or disorder is aneurysm or atherosclerosis.

In some embodiments the inhibitor is an oligonucleotide, a small molecule, a mimetic, a decoy, or an antibody. In some embodiments the antibody is a monoclonal antibody, a polyclonal antibody, a chimeric antibody, a humanized antibody, a single-chain antibody, or a Fab fragment. In some embodiments the inhibitor targets the vasculature, preferably the arterial system, more preferably the walls of the arterial system, and most preferably the media lamina in the vessel wall.

In some embodiments the inhibitor is a monoclonal antibody. In some embodiments the inhibitor is a monoclonal antibody that specifically binds to DP1 or DP2 receptor or to a MAP kinase. In some embodiments the antibody binds to DP1, DP2 or MAP kinase with an affinity of at least $1\times10^8$ Ka. In some embodiments the antibody has a binding affinity less than about $1\times10^5$ Ka for a polypeptide other than DP1. In some embodiments the antibody does not bind to DP2 receptor. In some embodiments the antibody is labeled with an enzyme, radioisotope, or fluorophore.

Methods of treatment comprise administering single or multiple doses of antibodies, small molecules, mimetics, decoy receptors, or oligonucleotides, or combinations and subcombinations of the above. In some embodiments the antibodies, small molecules, mimetics, decoy receptors, or oligonucleotides are administered as injectable pharmaceutical compositions that are sterile, pyrogen free and comprise the antibodies, small molecules, decoy receptors, mimetics or oligonucleotides in combination with a pharmaceutically acceptable carrier or diluent.

According to some aspects, the subject is treated with the antibodies, small molecules, mimetics, decoy receptors, or oligonucleotides in conjunction with conventional medicaments. For example, following administration of the antibodies, small molecules, mimetics, decoy receptors, or oligonucleotides, the patient may also be treated with a therapeutically effective amount of an anti-coagulant.

Combination Therapy

In some embodiments the methods further comprise the treatment of the subject with a traditional medicament for the treatment of a cardiovascular disease or disorder. In some preferred embodiments the cardiovascular disease or disorder is an aneurysm, preferably an aortic aneurysm.

Examples of drugs to be used in combination with the inhibitors of the present invention include, without limitation, cholestyramine, colestipol, nicotinic acid, gemfibrozil, probucol, atorvastatin, lovastatin, aspirin, ticlopidine, clopidogrel or anti-coagulants.

Inhibitors

According to another aspect, the present invention provides inhibitors of cardiovascular diseases and disorders, inhibitors of smooth muscle proliferation, inhibitors of DP1 and/or DP2 receptor, and inhibitors of MAP Kinase. Inhibitors include, without limitation, oligonucleotides, small molecules, mimetics, decoys, or antibodies. In some preferred embodiments the cardiovascular disease or disorder is an aneurysm, preferably an aortic aneurysm.

Oligonucleotides

In some embodiments, the inhibitor is an oligonucleotide. In some embodiments the oligonucleotide is an antisense or RNAi oligonucleotide. In some embodiments the oligonucleotide is complementary to a region, domain, portion, or segment of a gene correlated with the DP1 or DP2 receptor or with a MAP kinase. In some embodiments, the gene is complementary to a region, domain, portion, or segment of the DP1 receptor or MAP kinase. In some embodiments, the oligonucleotide comprises from about 5 to about 100 nucleotides, from about 10 to about 50 nucleotides, from about 12 to about 35, and from about 18 to about 25 nucleotides. In some embodiments, the oligonucleotide is at least 50%, at least 60%, at least 70%, at least 80%, at least 90%, at least 95%, at least 96%, at least 97%, at least 98%, at least 99%, or at least 100% homologous to a region, portion, domain, or segment of the DP1, DP2 receptor or MAP kinase gene. In some embodiments there is substantial sequence homology over at least 15, 20, 25, 30, 35, 40, 50, or 100 nucleotides of the DP1 or DP2 receptor or MAP kinase gene.

In some embodiments, the inhibitor is a double stranded RNA (dsRNA) molecule and works via RNAi (RNA interference). In some embodiments, one strand of the dsRNA is at least 50%, at least 60%, at least 70%, at least 80%, at least 90%, at least 95%, at least 96%, at least 97%, at least 98%, at least 99%, or at least 100% homologous to a region, portion, domain, or segment of the DP1 or DP2 receptor or MAP kinase gene. In some embodiments there is substantial sequence homology over at least 15, 20, 25, 30, 35, 40, 50, 100, 200, 300, 400, 500, or 1000 nucleotides of the DP1 or DP2 receptor or MAP kinase gene.

Antibodies

In some embodiments the inhibitor is an antibody. In some embodiments the antibody is specific to the N-terminus of the gene product of the DP1 or DP2 receptor or MAP kinase gene. In other embodiments, the antibody is specific to the C-terminus of the gene product of the DP1 or DP2 receptor or MAP kinase gene. In some embodiments, the antibody is specific to a region, domain, portion, or segment of the gene product of the DP1 or DP2 receptor or MAP kinase gene that is between the N- and C-termini of the protein. In some embodiments, the antibody is specific to a region that spans both the N-terminus and the region that is between the N- and C-termini. In other embodiments, the antibody is specific for a region that spans both the C-terminus and the region that is in between the N- and C-termini.

In some embodiments the binding affinity of the antibodies for the DP1 or DP2 receptor or for MAP kinase is at least $1 \times 10^6$ Ka. In some embodiments the binding affinity of DP1 or DP2 receptor or MAP kinase antibodies is at least $5 \times 10^6$ Ka, at least $1 \times 10^7$ Ka, at least $2 \times 10^7$ Ka, at least $1 \times 10^8$ Ka, or greater. Antibodies of the present invention may also be described or specified in terms of their binding affinity to a polypeptide of the invention. In some embodiments binding affinities include those with a Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{8}$ M, $10^{-8}$ M, $5 \times 10^9$ M, $10^{-9}$ M, $5 \times 10^{-10}$M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$M, $5 \times 10^{14}$ M, $10^{-14}$ M, $5 \times 10^{15}$ M, or $10^{-15}$ M, or less.

The invention also provides antibodies that competitively inhibit binding of an antibody to an epitope of the invention as determined by any method known in the art for determining competitive binding using, for example, immunoassays. In some embodiments, the antibody competitively inhibits binding to the epitope by at least 95%, at least 90%, at least 85%, at least 80%, at least 75%, at least 70%, at least 60%, or at least 50%.

Methods of predicting epitopes to which an antibody of the invention can bind are well-known to those of skill in the art and include without limitation, Kyte-Doolittle Analysis (Kyte, J. and Dolittle, R. F., J. Mol. Biol. (1982) 157:105-132), Hopp and Woods Analysis (Hopp, T. P. and Woods, K. R., Proc. Natl. Acad. Sci. USA (1981) 78:3824-3828; Hopp, T. J. and Woods, K. R., Mol. Immunol. (1983) 20:483-489; Hopp, T. J., J. Immunol. Methods (1986) 88:1-18), Jameson-Wolf Analysis (Jameson, B. A. and Wolf, H., Comput. Appl. Biosci. (1988) 4:181-186), and Emini Analysis (Emini, E. A., Schlief, W. A., Colonno, R. J. and Wimmer, E., Virology (1985) 140:13-20).

In some embodiments the antibody is selected from the group consisting of a monoclonal antibody, a humanized antibody, a chimeric antibody, a primatized antibody, a phage-displayed antibody, a single chain antibody, or a fragment of any of the preceding. In some preferred embodiments the antibody is a humanized antibody.

Antibodies of the present invention may act as agonists or antagonists of the polypeptides of the present invention. For example, in some embodiments the present invention provides antibodies which disrupt the receptor/ligand interactions with the polypeptides of the invention either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques known in the art. In some embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The present invention further provides receptor-specific antibodies which both prevent ligand binding and receptor activation as well as antibodies that recognize the receptor-ligand complex, and, in some embodiments, do not specifically recognize the unbound receptor or the unbound ligand.

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Suitable antibodies according to the present invention can recognize linear or conformational epitopes, or combinations thereof. Antibodies which recognize $PGD_2$ receptors, MAP kinases and cytokines are known to those skilled in the art.

The present invention also provides antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include, without limitation, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, or $^{99}Tc$.

In some embodiments the antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}Bi$. A cytotoxin or cytotoxic agent includes any agent that is detrimental to cells. Examples of cytotoxins or cytocidals include one or more of paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques for conjugating such therapeutic moieties to antibodies are well known to the art skilled, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

In addition to chimeric and humanized antibodies, fully human antibodies can derived from transgenic mice having human immunoglobulin genes (see, e.g., U.S. Pat. Nos. 6,075,181, 6,091,001, and 6,114,598, all of which are incorporated herein by reference), or from phage display libraries of human immunoglobulin genes (see, e.g McCafferty et al., Nature, 348:552-554 (1990). Clackson et al., Nature, 352: 624-628 (1991) and Marks et al., J. Mol. Biol., 222:581-597 (1991)).

Monoclonal antibodies can be prepared using the method of Kohler et al. (1975) Nature 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro or in vivo.

As an alternative to the use of hybridomas for expression, antibodies can be produced in a cell line such as a CHO or myeloma cell lines, as disclosed in U.S. Pat. Nos. 5,545,403; 5,545,405; and 5,998,144; incorporated herein by reference. Fragments of the antibodies are suitable for use in the methods of the invention as long as they retain the desired affinity and/or activity of the full-length antibody.

Antibodies or antibody fragments thereof may be conjugated prior to use in the methods of the present invention.

Methods for producing conjugated antibodies are known in the art. The antibody (or fragment thereof) may be conjugated to a therapeutic moiety such as a cytotoxin, a therapeutic agent, or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, interferon-alpha, interferon-beta, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating therapeutic moieties to antibodies are well known. See, for example, WO 2004010957 A2; Arnon et al. (1985) "Monoclonal Antibodies for Immunotargeting of Drugs in Cancer Therapy," in *Monoclonal Antibodies and Cancer Therapy*, ed. Reisfeld et al. (Alan R. Liss, Inc.), pp. 243-256; ed. Hellstrom et al. (1987) "Antibodies for Drug Delivery," in *Controlled Drug Delivery*, ed. Robinson et al. (2d ed; Marcel Dekker, Inc.), pp. 623-653; "Analysis, Results, and Future Prospective of the Therapeutic Use of Radiolabeled Antibody in Cancer Therapy," in *Monoclonal Antibodies for Cancer Detection and Therapy*, ed. Baldwin et al. (Academic Press, New York, 1985), pp. 303-316.

The term "specific for," when used to describe antibodies of the present invention, indicates that the variable regions of the antibodies of the invention recognize and bind target polypeptides exclusively by virtue of measurable differences in properties including binding affinity, despite the possible existence of localized sequence identity, homology, or similarity between the target protein and other polypeptides). Those skilled in the art readily understood that such specific antibodies may also interact with other proteins (for example, *S. aureus* protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art, as discussed in Harlow et al. (Eds.), Antibodies: A Laboratory Manual; Cold Spring Harbor Laboratory; Cold Spring Harbor, N.Y. (1988), Chapter 6.

Antibodies are defined to be "specifically binding" if: 1) they exhibit a threshold level of binding activity, and/or 2) they do not significantly cross-react with known related polypeptide molecules. The binding affinity of an antibody can be readily determined by one of ordinary skill in the art, for example, by Scatchard analysis (Scatchard, Ann. NY Acad. Sci. 51: 660-672, 1949). In some embodiments the antibodies of the present invention bind to their target epitopes or mimetic decoys at least $10^3$, at least $10^4$, at least $10^5$, and at least $10^6$ fold higher than to other known family members.

In some embodiments, the antibodies of the present invention do not specifically bind to known related polypeptide molecules, for example, if they bind DP1 receptor but not known DP2 (or vice versa) using a standard Western blot analysis (Ausubel et al.). Examples of known related polypeptides include, without limitation, other members of the $PGD_2$ receptor family and the like. In some embodiments antibodies may be screened against known related polypeptides to isolate an antibody population that specifically binds to a particular receptor. Screening and isolation of specific antibodies is well known in the art (see, Fundamental Immunology, Paul (eds.), Raven Press, 1993; Getzoff et al., Adv. in Immunol. 43: 1-98, 1988; Monoclonal Antibodies: Principles and Practice, Goding, J. W. (eds.), Academic Press Ltd., 1996; Benjamin et al., Ann. Rev. Immunol. 2: 67-101, 1984). Representative examples of such assays include: concurrent immunoelectrophoresis, radioimmunoassay (RIA), radioimmunoprecipitation, enzyme-linked immunosorbent assay (ELISA), dot blot or Western blot assay, inhibition or competition assay, and sandwich assay.

In some embodiments, the antibodies of the present invention have at least about 1000 fold, and at least about 10,000 fold greater affinity for DP1 or DP2 receptor or for MAP kinase than for known related family members. In some embodiments, the binding affinity of an antibody of the present invention is less than about $1 \times 10^5$ Ka, less than about $1 \times 10^4$ Ka, and preferably less than $1 \times 10^3$ Ka, for a related polypeptide other than DP1 or DP2 receptor or MAP kinase.

According to preferred embodiments of the invention, a monoclonal antibody is provided which has the following properties: (a) binds to DP1 or DP2 receptor and (b) inhibits aortic smooth muscle proliferation.

In some embodiments the antibodies bind to DP1 or DP2 receptor in a vessel wall. In some preferred embodiments the antibodies bind to the media lamina or intima.

Small Molecules

In some embodiments, the inhibitor is a small molecule. In some embodiments, the small molecule has a molecular weight that is less than about 9, about 8, about 7, about 6, about 5, about 4, about 3, about 2, or about 1 kilodalton. Small molecule inhibitors of $PGD_2$ receptors and/or MAP kinases are known to those skilled in the art.

Pharmaceutical Compositions

The present invention also provides pharmaceutical compositions comprising one or more of the inhibitors described herein and a pharmaceutically acceptable carrier. The term "pharmaceutically acceptable carrier" refers to a carrier for administration of a therapeutic agent, such as antibodies, oligonucleotides, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, lipid aggregates and inactive virus particles and are well known to those of skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles.

In some embodiments the pharmaceutical compositions are prepared as injectables, either as liquid solutions or suspensions; solid forms suitable for solution in, or suspension in, liquid vehicles prior to injection can also be prepared. In some preferred embodiments to pharmaceuticals are prepared as sterile injectables.

Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington: The Science and Practice of Pharmacy* (1995) Alfonso Gennaro, Lippincott, Williams, & Wilkins.

Generally, treatment with the methods and/or pharmaceutical compositions of the present invention is initiated with small dosages which can be increased by small increments until the optimum effect under the circumstances is achieved. In some embodiments, the inhibitor is an antagonistic inhibitor. In some embodiments, the inhibitor is an inhibitor of a biosynthetic enzyme. In some embodiments, the inhibitor is a disease inhibitor. The inhibitors can be administered in one dose, continuously or intermittently throughout the course of treatment. The inhibitors may be administered several times each day, once a day, once a week, or once every two weeks.

Administration of the inhibitors of the present invention can be carried out, for example, by inhalation or suppository or to mucosal tissue such as by lavage to vaginal, rectal, urethral, buccal and sublingual tissue, orally, topically, intranasally, intraperitoneally, parenterally, intravenously, intralymphatically, intratumorly, intramuscularly, interstitially, intra-arterially, subcutaneously, intraoccularly, intrasynovial, transepithelial, and transdermally. In preferred embodiments, the inhibitors are administered orally or inter-arterially. The inhibitors can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, all using dosage forms well known to those of ordinary skill in the pharmaceutical arts.

Methods for Identifying Inhibitors of Cardiovascular Diseases or Disorders

The present invention provides methods for identifying inhibitors of cardiovascular diseases or disorders. In some embodiments the methods comprise contacting $PGD_2$ or a $PGD_2$ agonist with a model system that comprises cells which express prostaglandin D2 receptors in the presence and absence of a candidate compound and determining whether the cardiovascular disease or disorder is inhibited, whether cell proliferation is affected, or whether expression levels of markers are reduced, or activation levels are reduced in the presence of the test compound relative to what occurs in its absence. In some embodiments the prostaglandin D2 receptor is DP1 or DP2. In some preferred embodiments the cardiovascular diseases or disorder is aneurysm or atherosclerosis. References describing this include Egan et al Circulation 2005 and Cheng et al Science 2002.

The candidate compound can be contacted with a $PGD_2$ or a $PGD_2$ agonist/or antagonist and a model system comprising prostaglandin D2 receptors by any means that is available that puts the compound in contact model system. In some embodiments, the compound is injected into the cell. If the cell is in an in vitro environment (e.g. cell culture) the test compound can be added to the media in which the cell is growing. The test compound can also be tested in vivo by administering the test compound to a subject. The test compound can be administered by any means available including, but not limited to, injection, orally, and the like.

In some embodiments, determining whether inhibition of a cardiovascular disease or disorder is achieved via known diagnostic methods including, without limitation, measuring abnormal differences between the blood pressure of the ankle and arm, Doppler studies, ultrasonic Duplex scanning, CT scans, magnetic resonance arteriography (MRA), arteriography, intravascular ultrasound (IVUS), and cardiac stress testing. In some preferred embodiments, determining whether a cardiovascular disease or disorder is inhibited is achieved by measuring DP1 or DP2 levels, by measuring induction of MAP kinase, or by measuring smooth muscle cell proliferation, wherein induction of MAP kinase is indicative of a compound that is not an inhibitor of a cardiovascular disease or disorder, and reduction of DP1 or DP2 levels or inhibition of smooth muscle cell proliferation is indicative of a compound that is an inhibitor of a cardiovascular disease or disorder.

In some embodiments the model system comprises a transgenic mouse. In some embodiments the transgenic mouse has a genotype of LDL $R^{-/-}$. In some embodiments the transgenic mouse has a genotype of DP1$^{-/-}$. In some embodiments the transgenic mouse has a genotype of LDL $R^{-/-}$/DP1$^{-/-}$. Methods of creating a cell or animals that are deficient in the expression of a particular gene or set of genes are known in the art. Examples include, but are not limited to those described in U.S. Patent Application 20030091982, siRNA, antisense oligonucleotides, and the like.

In some embodiments the transgenic mouse is fed a diet high in lipids. In some embodiments the transgenic mouse is fed a diet with lipids at a normal level. In some embodiments the transgenic mouse is fed a diet low in lipids.

In some embodiments the model system comprises one or more samples. In some preferred embodiments, the model system comprises cells or tissues from the vasculature.

In some embodiments the methods comprise contacting more than one candidate compound in parallel. In some embodiments, the methods comprises contacting 2, 3, 4, 5, 6, 7, 8, 9, 10, 15, 20, 25, 30, 40, 50, 100, 1000, at least 2, at least 5, at least 10, at least 50, at least 100, or at least 1000 candidate compounds in parallel. In some embodiments, the present invention uses High Throughput Screening (HTS) of compounds. In some embodiments the present invention assays partial or complete combinatorial libraries. Those of skill in the art are familiar with methods of screening candidate compounds. The methods can also be automated such that a robot can perform the experiments. The present invention can also be adapted for the screening of large numbers of compounds, such as combinatorial libraries of compounds. Indeed, compositions and methods allowing efficient and simple screening of several compounds in short periods of time are provided. The instant methods can be partially or completely automated, thereby allowing efficient and simultaneous screening of large sets of compounds.

In some embodiments, the screening methods of the present invention comprise the step of contacting a cell in the presence of a test compound. The cells can then be observed to determine if the candidate compound inhibits, inter alia, a cardiovascular disease or disorder by detecting smooth muscle proliferation, MAP kinase activation, cytokine expression, and the like. A control may be provided in which the cell is not contacted with a candidate compound. For example, if the cells contacted with the candidate compound inhibit smooth muscle proliferation, inhibit activation of MAP kinase, or inhibit cytokine expression, anti-cardiovascular disease activity is indicated for the candidate compound.

Positive and negative controls may be performed in which known amounts of candidate compound and no compound, respectively, are added to the assay. One skilled in the art would have the necessary knowledge to perform the appropriate controls. In some embodiments, varying amounts of compounds with known activity may be tested.

The candidate compound can be any product in isolated form or in mixture with any other material (e.g., any other product(s)). The candidate compound may be defined in terms of structure and/or composition, or it may be undefined. For instance, the compound may be an isolated and structurally-defined product, an isolated product of unknown structure, a mixture of several known and characterized products or an undefined composition comprising one or several products. Examples of such undefined compositions include for instance tissue samples, biological fluids, cell supernatants, vegetal preparations, etc. The candidate compound may be any organic or inorganic product, including a polypeptide (or a protein or peptide), a nucleic acid, a lipid, a polysaccharide, a chemical product, or any mixture or derivatives thereof. The compounds may be of natural origin or synthetic origin, including libraries of compounds.

In some embodiments, the activity of the test compound(s) is unknown, and the method of this invention is used to identify compounds exhibiting the selected property (e.g., inhibition of smooth muscle proliferation). However, in some embodiments instances where the activity (or type of activity) of the candidate compound(s) is known or expected, the method can be used to further characterize the activity (in terms of specificity, efficacy, etc.) and/or to optimize the activity, by assaying derivatives of the candidate compounds.

The amount (or concentration) of candidate compound can be adjusted by the user, depending on the type of compound (its toxicity, cell penetration capacity, etc.), the number of cells, the length of incubation period, etc. In some embodiments, the candidate compound can be contacted in the presence of an agent that facilitates penetration or contact with the cells. The candidate compound is provided, in some embodiments, in solution. Serial dilutions of test compounds may be used in a series of assays. In some embodiments, candidate compound(s) may be added at concentrations from 0.01 µM to 1M. In some embodiments, a range of final concentrations of a candidate compound is from 10 µM to 100 µM.

Those skilled in the art are familiar with assays to determine, for example, levels of smooth muscle proliferation, inhibition of MAP kinase activation, inhibition of MAP kinase, and inhibition of cytokine expression.

In some embodiments the present invention provides methods for identifying inhibitors of cardiovascular disease or disorders. The methods comprise contacting prostaglandin D2 receptor agonist with a model system comprising prostaglandin D2 receptors in the presence and absence of a candidate compound and determining whether aortic smooth muscle cell proliferation is inhibited. Inhibition of aortic smooth muscle cell proliferation activity is indicative of an inhibitor of a cardiovascular disease or disorders. In some embodiments the cardiovascular disease or disorders is selected form the group consisting of aneurysm, atherosclerosis, hypertension, and stroke.

In some embodiments the present invention provides methods for identifying inhibitors of aneurysm or atherosclerosis. The methods comprise contacting a prostaglandin D2 receptor agonist with a model system comprising prostaglandin D2 receptors in the presence and absence of a candidate compound and determining whether aortic smooth muscle cell proliferation is inhibited. Inhibition of aortic smooth muscle cell proliferation activity is indicative of an inhibitor of aneurysm or atherosclerosis. In some embodiments the prostaglandin D2 receptor agonist is prostaglandin D2. In some embodiments the prostaglandin D2 receptors is DP1 or DP2.

In some embodiments the present invention provides methods for identifying inhibitors of aneurysm or atherosclerosis and/or the proliferative response to vascular injury. The methods comprise contacting a prostaglandin D2 receptor agonist with a model system comprising prostaglandin D2 receptors in the presence and absence of a candidate compound and determining whether cytokine expression and/or plaque burden is inhibited. Inhibition of cytokine expression is indicative of an inhibitor of aneurysm or atherosclerosis. In some embodiments the prostaglandin D2 receptor agonist is prostaglandin D2. In some embodiments the prostaglandin D2 receptor is DP1 or DP2.

The present invention also provides methods for identifying inhibitors of cardiovascular disease or disorders comprising contacting PGD2 or a PGD2 agonist with a cell expressing DP1 receptor in the presence and absence of a candidate compound and determining whether DP1 and/or DP2 expression or activity is inhibited, wherein inhibition of DP1 and/or DP2 expression or activity is indicative of an inhibitor of cardiovascular disease or disorders. In some preferred embodiments the cardiovascular diseases or disorder is aneurysm or atherosclerosis.

In some embodiments the methods further comprise the optional step of determining selectivity of the inhibitor. The optional step comprises determining whether the candidate compound inhibits one or more of aortic smooth muscle cell proliferation, MAP kinase activity or activation, or cytokine expression in a second model system comprising cells derived from lung comprising prostaglandin D2 receptors, wherein the inhibition of one or more of one or more of aortic smooth muscle cell proliferation, MAP kinase activity or activation, or cytokine expression in the second model system is indicative of a non-specific inhibitor.

In some embodiments the methods further comprise the optional step of determining selectivity of the inhibitor. The optional step comprises determining whether the candidate compound inhibits one or more of aortic smooth muscle cell proliferation, MAP kinase activity or activation, or cytokine expression in a second model system. The model system comprises cells isolated from or derived from the media lamina or intima and the second model system comprises cells not isolated or derived from media lamina or intima, wherein the inhibition of one or more of one or more of aortic smooth muscle cell proliferation, MAP kinase activity or activation, or cytokine expression in the first model system but not in the second model system is indicative of a specific inhibitor.

Diagnostic Methods

The present invention also provides diagnostic methods for cardiovascular disease or disorders. In some preferred embodiments the cardiovascular disease or disorder is aneurysm or atherosclerosis.

In some embodiments the methods comprise imaging atherosclerotic plaques. The imaging methods comprise administering a probe, antibody or oligonucleotide that binds to one or more components of the DP1 and/or DP2 receptor. In some embodiments the probe, antibody or oligonucleotide is detectably labeled. In some embodiments, binding of the probe, antibody or oligonucleotide to DP1 and/or DP2 receptor is indicative of the presence of one or more atherosclerotic plaques. In some embodiments the antibody is a labeled monoclonal antibody. In some embodiments the antibody binds to the media lamina or intima layer of the vasculature. In some embodiments the imaging method is used to monitor the progression or regression of a cardiovascular disease or disorder. In some embodiments the subject is a human having or suspected of having atherosclerotic disease.

The present invention also provides methods of developing a prognosis for a subject who has been diagnosed with a cardiovascular disease or disorder comprising measuring levels of DP1 and/or DP2 in a sample from the subject and comparing the DP1 and/or DP2 levels to the DP1 and/or DP2 levels found in control subjects. In some embodiments the control subjects are free of cardiovascular disease or disorder. In some embodiments the DP1 and/or DP2 levels are mRNA or protein levels. In some embodiments, a ratio of DP1/DP2 levels is generated and compared to a control ratio. In some preferred embodiments the cardiovascular disease or disorder is aneurysm or atherosclerosis.

The present invention further provides methods of identifying subjects at risk for cardiovascular disease or disorders. The methods comprise measuring levels of DP1 and/or DP2 in a sample from a subject and comparing the DP1 and/or DP2 levels to DP1 and/or DP2 levels found in normal subjects, wherein elevated levels of DP1 and/or DP2 are indicative of an increased risk for cardiovascular disease or disorder. In some embodiments the DP1 and/or DP2 levels are mRNA or protein levels. In some preferred embodiments the cardiovascular disease or disorder is aneurysm or atherosclerosis.

Some of the preferred embodiments of the invention described above are outlined herein. As those skilled in the art will appreciate, numerous changes and modifications may be made to the preferred embodiments of the invention without departing from the spirit of the invention. It is intended that all such variations fall within the scope of the invention. The entire disclosure of each publication cited herein is hereby incorporated by reference.

EXAMPLES

Example 1

Tissue Distribution of DP1 and DP2 mRNA in Hyperlipidemic Mice

To investigate the potential tissue-specific roles of DP1 and DP2 in atherosclerosis, DP1 and DP2 expression in a mouse model of atherosclerosis (apoE–/–) was surveyed using real-time RT-PCR. The mice were fed with chow diet (8 months, n=3. For DP1, of all tissues surveyed, the highest mRNA expression level was found in lung, followed by spleen, aorta, muscle, brain and ileum (FIG. 1A). DP2 is highly expressed in lung, but relatively low in all other tissues examined (FIG. 1B). Both DP1 and DP2 are detectable but expressed at low level in heart (FIGS. 1A and 1B). This is the first time that both DP1 and DP2 expression were documented in the vasculature of hyperlipidemic mice.

Example 2

DP1 and DP2 mRNA Expression in Aorta of Hyperlipidemic Mice

Figure 2:
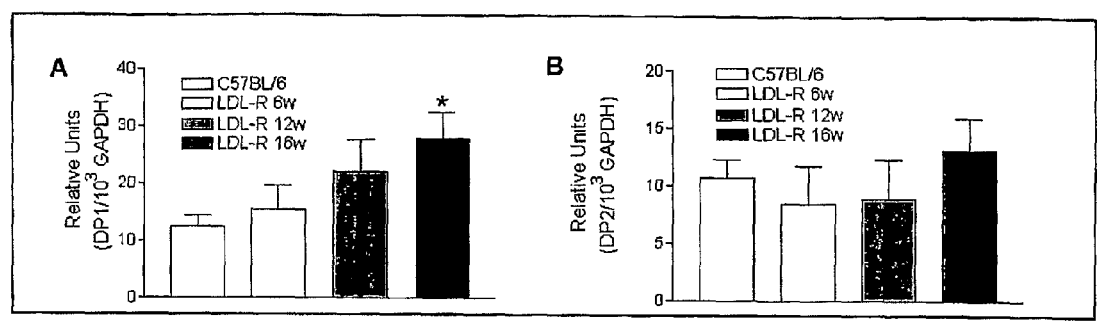
FIG. 2 depicts aortic DP1 (A) and DP2 (B) mRNA expression. LDL-R 6 w, 12 w and 16 w: LDL-R$^{-/-}$ mice on Western diet for 6, 12 and 16 weeks. (*: P<0.05 vs C57BL/6. Data are presented as mean±SEM, n=3).

Aortic expression of DP1 and DP2 was verified in a second mouse model of atherosclerosis (LDL-R–/– strain). The levels were assessed in mice on Western diet for 6, 12 and 16 weeks (*; P, 0.05 vs C57BL/6. Data are presented as mean+/–SEM, n=3) Increased mRNA levels of aortic DP1 transcripts were observed in LDL-R–/– mice as the disease progresses (FIG. 2A). DP1 expression was significantly increased in LDL-R–/– mice on Western diet for 16 weeks compared to C57BL/6 mice (FIG. 2A) while there is no significant change of the aortic DP2 expression as the disease advances (FIG. 2B).

Example 3

Expression of DP1 and DP2 in the Lamina Media of Aorta in LDL-R–/– Mice

Figure 3:
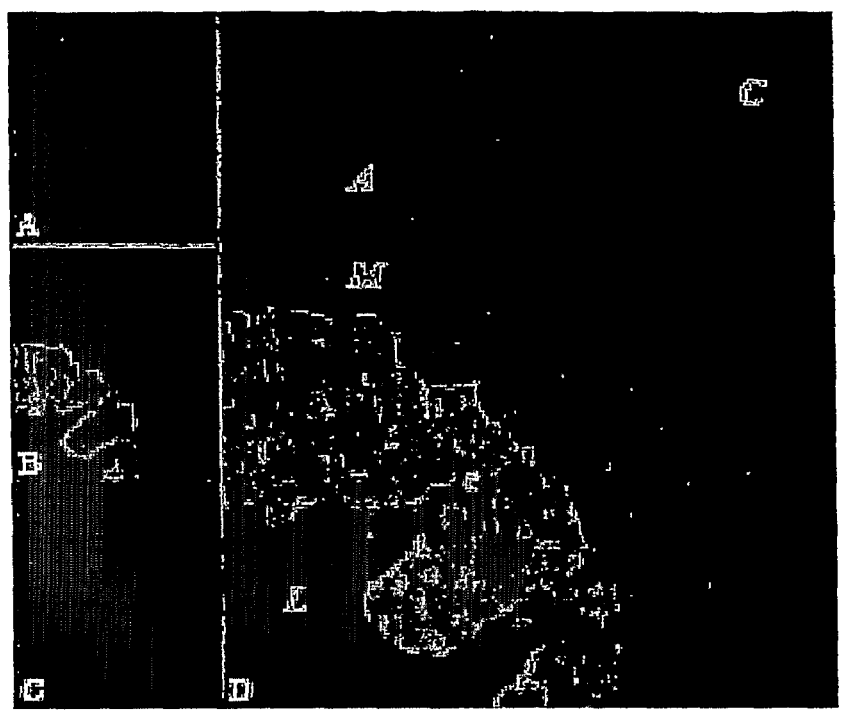
FIG. 3 depicts DP1 expression in aortic root section of LDL-R$^{-/-}$ mouse on Western diet for 12 weeks. Immunofluorescent staining of DNA (A), DAPI blue; CD68 (B), FITC green; DP1 (C), cy3 red, white arrows indicate DP1$^+$ cells in the media; merge of DP1, CD68 and DNA (D). L: lumen; I: Intima; M: Media; A: Adventitia. C: Coronary artery. Representative micrograph was obtained by using Laser Confocal microscopy. (magnification: 250 fold)
Figure 4:
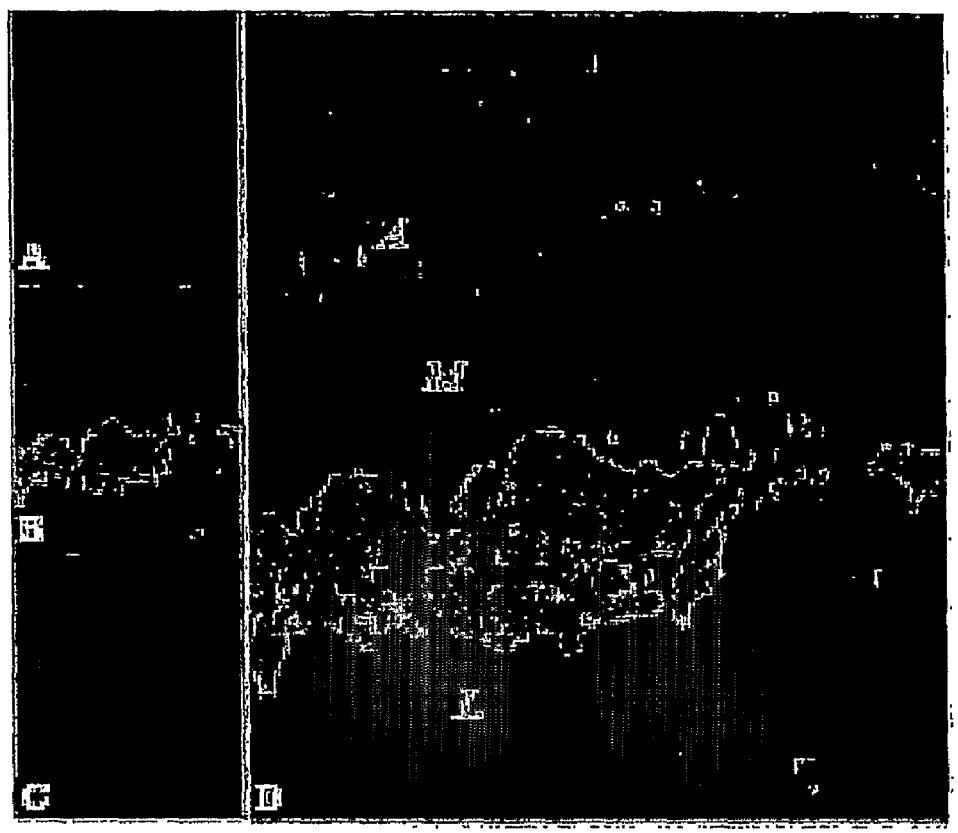
FIG. 4 depicts DP2 expression in aortic root section of LDL-R$^{-/-}$ mouse on Western diet for 12 weeks. Immunofluorescent staining of DNA (A), DAPI blue; CD68 (B), FITC green; DP2 (C), cy3 red, white arrows indicate DP2$^+$ cells in the media and the shoulder area of the plaque; merge of DP2, CD68 and DNA (D). L: lumen; I: Intima; M: Media; A: Adventitia. Representative micrograph was obtained by using Laser Confocal microscopy. (magnification: 250 fold)

To further explore the cellular location of aortic DP1 and DP2 expression, the expression of DP1 and DP2 in the arterial wall of LDL-R–/– mice on Western diet (Harlan-Teklad 88137) for 12 weeks was measured using immuofluorescent staining. FIG. 3A shows DNA stained with DAPI. FIG. 3B shows CD68 stained with FITC. FIG. 3C shows DP1 stained with cy3. FIG. 3D shows a merge of DNA stained with DAPI, CD68 stained with FITC and DP1 stained with cy3DP1. White arrows indicate DP1+ cells in the media. L indicates Lumen; I indicates Intimal; M indicates media; A indicates Adventitia; C indicates coronary artery. DP1 was preferentially expressed in the aortic lamina media, yet rarely expressed in the intima and adventitia (FIG. 3C and 3D). The DP1+ staining does not co-localize with the CD68+ staining, a marker of distinct macrophage populations, which is highly expressed in intimal foam cells (FIGS. 3B and 3D). Similar expression pattern of DP2 was observed in the aortic lamina media. FIG. 4A shows DNA stained with DAPI. FIG. 4B shows CD68 stained with FITC. FIG. 4C shows DP1 stained with cy3. FIG. 4D shows a merge of DNA stained with DAPI, CD68 stained with FITC and DP1 stained with cy3DP1. White arrows indicate DP2+ cells in the media. L indicates Lumen; I indicates Intimal; M indicates media; A indicates Adventitia; C indicates coronary artery. The fluorescent signal of DP2 is relatively weaker than that of DP1. In addition, weak DP2+ staining was also observed at the shoulder area of the atherosclerotic plaque (FIG. 4D).

Example 4

Generation of LDLR–/–/DP2–/– Mice

Figure 5:
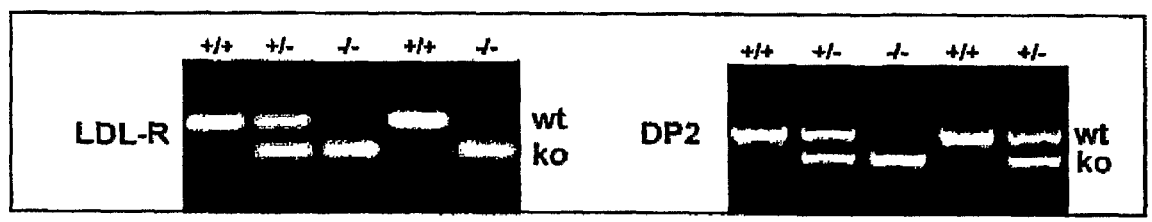
FIG. 5 depicts PCR Genotyping of LDL-R$^{-/-}$ and DP2$^{-/-}$ mice.

We have obtained DP2–/– mice from Dr. Beverly Koller and initiated a cross of these animals into LDLR–/– mice (FIG. 5). So far, LDL-R+/–/DP2+/– breeders have been obtained.

Example 5

Figure 6:
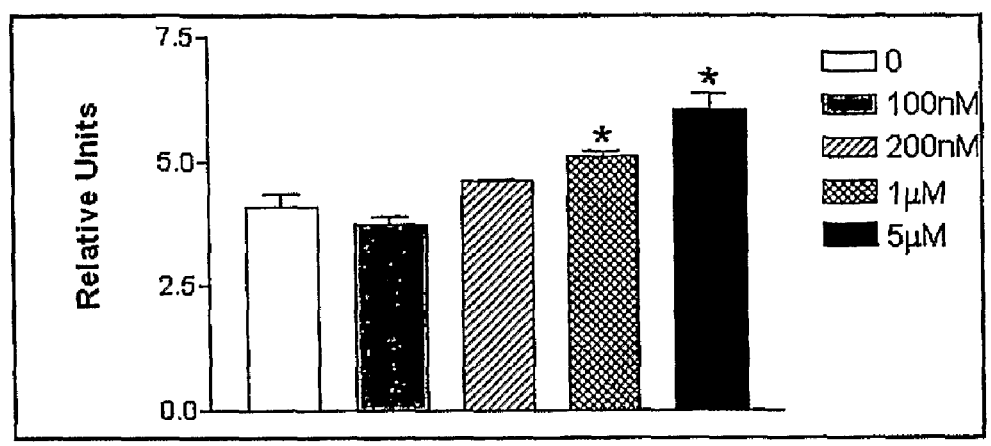
FIG. 6 depicts the effect of PGD$_2$ on mASMC proliferation. Confluent, quiescent SMC were treated with varies concentrations of PGD$_2$. Cell proliferation was determined by MTT assay at 24 hr. Values are mean±S.E.M. (*: P<0.005, by One-way ANOVA and t test, n=6).

$PGD_2$ Stimulates Mouse Aortic Smooth Muscle Cell (mASMC) Proliferation In Vitro The effect of $PGD_2$ on mASMC proliferation was determined by MTT assay. The results demonstrated that the addition of $PGD_2$ (1 and 5 µM) significantly promote mASMC proliferation at 24 hr (FIG. 6).

Example 6

$PGD_2$ Activates MAPK Activity in mASMC In Vitro

Figure 7:
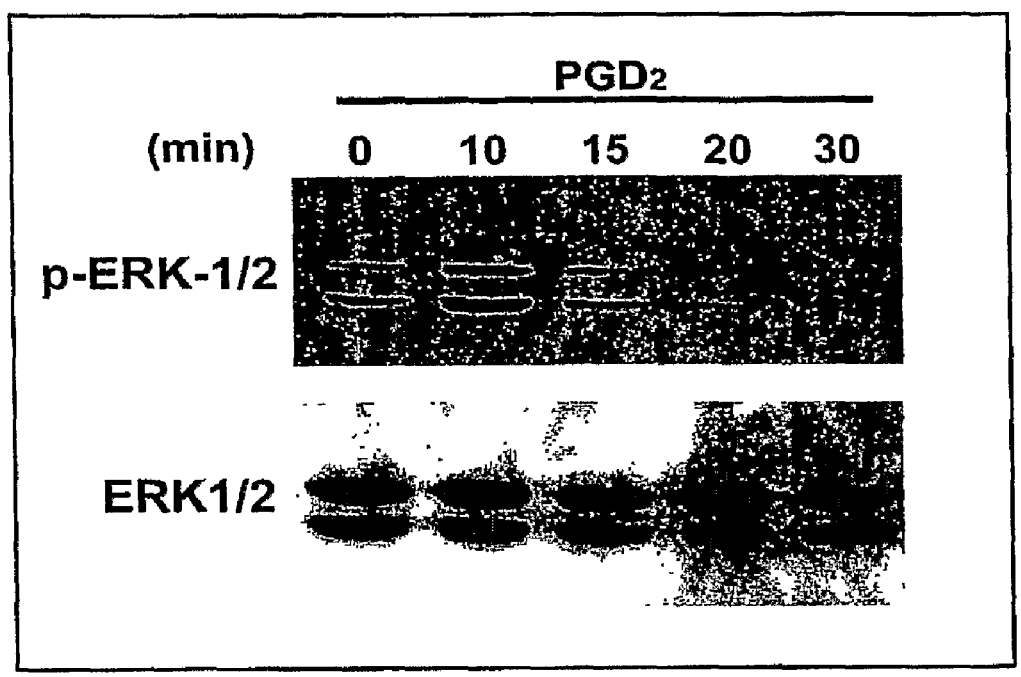
FIG. 7 depicts the effect of PGD$_2$ on MAPK activation in mASMC. Confluent, quiescent SMC were treated with 1 μM PGD$_2$ for varies timepoints. Cells were lysed and the lysate was analyzed for phosphorylated ERK1/2 (upper panel) and MARK (lower panel) by Western analysis, using antibodies to phosphotyrosine –ERK1/2 and ERK1/2, respectively.

The effect of $PGD_2$ on activation of MAP Kinase (MAPK) was tested by Western analysis of SMC lysate. The data indicated the induction of a phosphorylated-MAPK1/2 (molecular mass of 44 and 42 kDa) in PGD$_2$-treated cells as early as 10 min, the level of which returned to control levels after 15 min (FIG. 7). These data demonstrate that PGD$_2$-induced mASMC proliferation may be dependent on activation of MAPK.

Example 7

Sequences

Sequences for the DP1 receptor are known in the art (see, for example, Accession No. NM_008962) and are discussed, for example, in Hirata et al., Proc Natl Acad Sci U S A. 1994 Nov. 8; 91(23):11192-6), each of which is herein incorporated by reference in its entirety. SEQ ID NO:1 shows a nucleic acid sequence that encodes DP1 receptor. SEQ ID NO:2 shows an amino acid sequence of DP1 receptor.

DP1 Receptor

Sequences for the DP2 receptor are also known (see, for example, Accession No. NM_000953) and are discussed, for example, in Boie et al. (J Biol Chem. 1995 Aug. 11; 270(32): 18910-6), each of which is herein incorporated by reference in its entirety. SEQ ID NO:3 shows a nucleic acid sequence that encodes DP2 receptor. SEQ ID NO:4 shows an amino acid sequence of DP2 receptor.

Example 8

Figure 8:
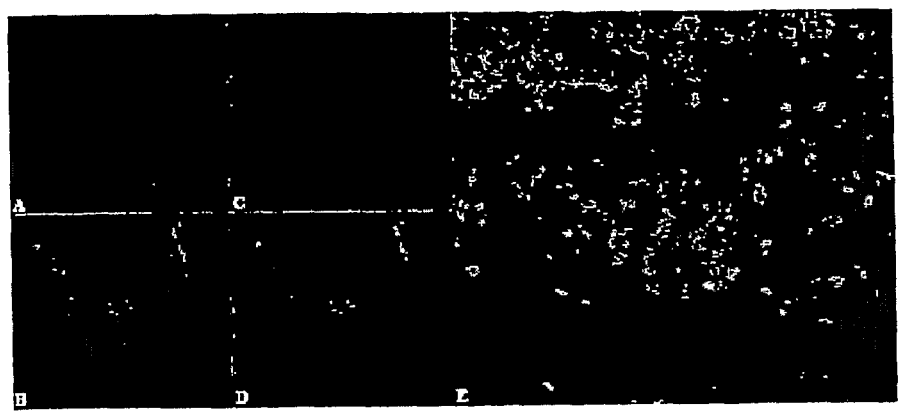
FIG. 8 depicts DP1 expression in abdominal aortic aneurismal tissue from apoE$^{-/-}$ infused with angiotensin II.

DP1 expression in abdominal aortic aneurismal tissue from apoE$^{-/-}$ infused with angiotensin II was evaluated. FIG. 8A shows DNA stained with DAPI. FIG. 8B shows CD68 stained with FITC. FIG. 8C shows DP1 stained with cy3. FIGS. 8D and 8E show a merge of DNA stained with DAPI, CD68 stained with FITC and DP1 stained with cy31.

What is claimed is:

1. A method for identifying whether a compound inhibits proliferation of vascular smooth muscle cells in response to vascular injury comprising
    contacting, in the presence of a candidate compound, aortic smooth muscle cells that express prostaglandin D2 receptors with an amount of a prostaglandin D2 receptor agonist effective to activate MAP kinase activity in said aortic smooth muscle cells in the absence of the candidate compound, and
    determining whether activation of MAP kinase activity in the aortic smooth muscle cells contacted with the prostaglandin D2 agonist in the presence of the candidate compound is inhibited compared to activation of MAP kinase activity in the aortic smooth muscle cells contacted with the prostaglandin D2 agonist in the absence of the candidate compound,
    wherein inhibition of activation of the MAP kinase activity in the presence of the candidate compound compared to activation of MAP kinase activity indicates that the candidate compound is an inhibitor of the proliferation of vascular smooth muscle cells in response to vascular injury and
    wherein
    the prostaglandin D2 receptor agonist is prostaglandin D2 or a biologically active metabolite of prostaglandin D2, and
    the prostaglandin D2 receptor is a prostaglandin D2 receptor that has an amino acid sequence at least 90% identical to SEQ ID NO:2 or SEQ ID NO:4 which when expressed in cells in the presence of prostaglandin D2 results in MAP kinase activity.

2. The method of claim 1 further comprising determining whether the candidate compound is a non-specific inhibitor of MAP kinase activity or activation in cells derived from lung, wherein said cells comprise prostaglandin D2 receptors, wherein the inhibition of MAP kinase activity or activation in the second model system indicates that the candidate compound is a non-specific inhibitor.

3. The method of claim 1 wherein the prostaglandin D2 receptor agonist is prostaglandin D2 or 15-deoxy Δ12,14 PG J2.

4. The method of claim 3 wherein the prostaglandin D2 agonist is 15-deoxy Δ12,14 PG J2.

5. The method of claim 1 wherein the aortic smooth muscle cells express SEQ ID NO:2, or SEQ ID NO:4, or SEQ ID NO:2 and SEQ ID NO:4.

6. The method of claim 5 wherein the aortic smooth muscle cells are aortic smooth muscle cells of a transgenic mouse that has a genotype selected from the group consisting of: LDL R$^{-/-}$; DPI$^{-/-}$; DP2$^{-/-}$; LDL R$^{-/-}$/DPI$^{-/-}$; and ApoE$^{-/-}$.

7. A method for identifying whether a compound inhibits proliferation of vascular smooth muscle cells in response to vascular injury comprising
    contacting, in the presence of a candidate compound, aortic smooth muscle cells that express prostaglandin D2 receptors with an amount of a prostaglandin D2 receptor agonist effective to activate MAP kinase activity in said aortic smooth muscle cells in the absence of the candidate compound, and
    determining whether activation of MAP kinase activity in the aortic smooth muscle cells contacted with the prostaglandin D2 agonist in the presence of the candidate compound is inhibited compared to activation of MAP kinase activity in the aortic smooth muscle cells contacted with the prostaglandin D2 agonist in the absence of the candidate compound,
    wherein inhibition of activation of the MAP kinase activity in the presence of the candidate compound compared to activation of MAP kinase activity indicates that the candidate compound is an inhibitor of the proliferation of vascular smooth muscle cells in response to vascular injury, and
    wherein the prostaglandin D2 receptor agonist is prostaglandin D2 or a biologically active metabolite of prostaglandin D2, and the prostaglandin D2 receptor is SEQ ID NO:2, or SEQ ID NO:4 which when expressed in cells in the presence of prostaglandin D2 results in MAP kinase activity.

8. The method of claim 1 wherein the receptor has an amino acid sequence at least 95% identical to SEQ ID NO:2 or SEQ ID NO:4.

9. The method of claim 1 wherein the receptor has an amino acid sequence at least 90% identical to SEQ ID NO:2.

10. The method of claim 1 wherein the receptor has an amino acid sequence at least 90% identical to SEQ ID NO:4.

11. The method of claim 1 wherein the receptor has an amino acid sequence at least 95% identical to SEQ ID NO:2.

12. The method of claim 1 wherein the receptor has an amino acid sequence at least 95% identical to SEQ ID NO:4.

13. The method of claim 1 wherein the receptor has an amino acid sequence identical to SEQ ID NO:2.

14. The method of claim 13 wherein the prostaglandin D2 receptor agonist is prostaglandin D2.

15. The method of claim 1 wherein the receptor has an amino acid sequence identical to SEQ ID NO:4.

16. The method of claim 15 wherein the prostaglandin D2 receptor agonist is prostaglandin D2.

17. The method of claim 3 wherein the prostaglandin D2 receptor agonist is prostaglandin D2.

18. The method of claim 8 wherein the prostaglandin D2 receptor agonist is prostaglandin D2 or 15-deoxy Δ12,14 PG J2.

19. A method for identifying whether a compound selectively inhibits proliferation of media lamina aortic smooth muscle cells in response to vascular injury comprising
    contacting, in the presence of a candidate compound, a first model system comprising aortic smooth muscle cells isolated or derived from media lamina that express prostaglandin D2 receptors with an amount of a prostaglandin D2 receptor agonist effective to activate MAP kinase activity in said aortic smooth muscle cells in the absence of the candidate compound,
    contacting, in the presence of a candidate compound, a second model system comprising aortic smooth muscle cells not isolated or derived from media lamina or that express prostaglandin D2 receptor agonist with an amount of a prostaglandin D2 receptor agonist effective to activate MAP kinase activity in said aortic smooth muscle cells in the absence of the candidate compound, and determining whether activation of MAP kinase activity in the aortic smooth muscle cells isolated or derived from media lamina of the first model system is inhibited compared to activation of MAP kinase activity level in the aortic smooth muscle cells not isolated or derived from media lamina or intima of the second model system, wherein inhibition by the candidate compound of activation of MAP kinase activity in the cells in the first model system but not in the second model system indicates that the candidate compound is a specific inhibitor of proliferation of media lamina aortic smooth muscle cells in response to vascular injury;

wherein the prostaglandin D2 receptor agonist is prostaglandin D2 or a biologically active metabolite of prostaglandin D2, and the prostaglandin D2 receptor is a prostaglandin D2 receptor that has an amino acid sequence at least 90% identical to SEQ ID NO:2 or SEQ ID NO:4 which when expressed in cells in the presence of prostaglandin D2 results in MAP kinase activity.

20. The method of claim 19 wherein the proliferation of media lamina aortic smooth muscle cells in response to vascular injury is proliferation of media lamina aortic smooth muscle cells in response to vascular injury of angioplasty.

21. The method of claim 1 wherein the proliferation of vascular smooth muscle cells in response to vascular injury is a proliferation of vascular smooth muscle cells in response to vascular injury of angioplasty.

22. The method of claim 7 wherein the proliferation of vascular smooth muscle cells in response to vascular injury is a proliferation of vascular smooth muscle cells in response to vascular injury of angioplasty.

23. The method of claim 1 wherein the proliferation of vascular smooth muscle cells in response to vascular injury is proliferation of vascular smooth muscle cells in a blood vessel.

24. The method of claim 7 wherein the proliferation of vascular smooth muscle cells in response to vascular injury is proliferation of vascular smooth muscle cells in a blood vessel.

25. The method of claim 19 wherein the proliferation of media lamina aortic smooth muscle cells in response to vascular injury is a proliferation of media lamina aortic smooth muscle cells in a blood vessel.

* * * * *

UNITED STATES PATENT AND TRADEMARK OFFICE
CERTIFICATE OF CORRECTION

PATENT NO. : 8,165,517 B2  
APPLICATION NO. : 11/814360  
DATED : April 24, 2012  
INVENTOR(S) : Fitzgerald and Zhao Page 1 of 1

It is certified that error appears in the above-identified patent and that said Letters Patent is hereby corrected as shown below:

Column 36, line 23, claim 25, "cular injury is a proliferation of media lamina aortic smooth" should read -- cular injury is proliferation of media lamina aortic smooth --.

Signed and Sealed this  
Eleventh Day of December, 2012

David J. Kappos  
*Director of the United States Patent and Trademark Office*